(12) United States Patent
Gunther et al.

(10) Patent No.: US 12,171,472 B2
(45) Date of Patent: Dec. 24, 2024

(54) TENSION BAND SYSTEMS AND METHODS

(71) Applicants: Stephen B. Gunther, Keswick, VA (US); Robert Glen Coleman, Eads, TN (US)

(72) Inventors: Stephen B. Gunther, Keswick, VA (US); Robert Glen Coleman, Eads, TN (US)

( * ) Notice: Subject to any disclaimer, the term of this patent is extended or adjusted under 35 U.S.C. 154(b) by 100 days.

(21) Appl. No.: 17/991,246

(22) Filed: Nov. 21, 2022

(65) Prior Publication Data

US 2023/0092603 A1     Mar. 23, 2023

Related U.S. Application Data

(63) Continuation of application No. 17/396,107, filed on Aug. 6, 2021, now Pat. No. 11,504,170.

(60) Provisional application No. 63/065,188, filed on Aug. 13, 2020.

(51) Int. Cl.
    *A61B 17/72*          (2006.01)
    *A61B 17/68*          (2006.01)

(52) U.S. Cl.
    CPC ...... *A61B 17/7225* (2013.01); *A61B 17/7208* (2013.01); *A61B 2017/681* (2013.01)

(58) Field of Classification Search
    CPC . A61B 17/72; A61B 17/7216; A61B 17/7225; A61B 17/7208; A61B 2017/681

USPC ........................................................ 606/62
See application file for complete search history.

(56) References Cited

U.S. PATENT DOCUMENTS

| | | | |
|---|---|---|---|
| 11,504,170 B2 * | 11/2022 | Gunther | A61B 17/7233 |
| 2009/0306718 A1 * | 12/2009 | Tipirneni | A61B 17/8685 |
| | | | 606/264 |

\* cited by examiner

*Primary Examiner* — Eduardo C Robert
*Assistant Examiner* — Christina Negrellirodriguez
(74) *Attorney, Agent, or Firm* — David Meibos; Maywood IP Law

(57) ABSTRACT

A bone fixation assembly may include an elongate fixation member and a flexible tensioning element. The elongate fixation member may include a central longitudinal axis, a distal portion couplable to a first bone fragment of a bone, and a proximal portion couplable to a second bone fragment of the bone to provide fixation of the second bone fragment relative to the first bone fragment. The flexible tensioning element may be couplable to the proximal and distal portions of the elongate fixation member to secure the elongate fixation member to the bone. The flexible tensioning element may be configured to span a bone fracture intermediate the first bone fragment and the second bone fragment to preload the bone fracture in compression to resist tensile force imparted across the bone fracture, thereby maintaining fixation of the first bone fragment relative to the second bone fragment.

17 Claims, 28 Drawing Sheets

TENSION BAND SYSTEMS AND METHODS

CROSS-REFERENCE TO RELATED APPLICATIONS

This application is a continuation of U.S. patent application Ser. No. 17/396,107 filed on Aug. 6, 2021, entitled "Tension Band Systems and Methods", which claims the benefit of U.S. Provisional Patent Application Ser. No. 63/065,188 filed on Aug. 13, 2020, entitled "Tension Band Systems and Methods". The foregoing are incorporated by reference as though set forth herein in their entirety.

TECHNICAL FIELD

The present disclosure relates to surgical implants, systems, and methods. More specifically, the present disclosure relates to surgical implants, systems, and methods related to bone fracture repair.

BACKGROUND

Bone fractures may be reduced and repaired with many different types of orthopedic internal fixation devices, systems, and methods. Two common types of orthopedic internal fixation devices include intramedullary rods and bone plates.

Intramedullary rods and bone plates each have their own particular advantages and disadvantages. For example, intramedullary rods typically require smaller incision sites and have less or no prominence in comparison to bone plates. Both of these characteristics may be desirable from a cosmetic perspective. Intramedullary rods usually cause fewer disturbances to surrounding soft tissues (e.g., less/no soft tissue stripping/irritation) in comparison to bone plates, reducing the risk of complications that may develop after surgery.

On the other hand, a bone plate may provide better structural integrity for certain types of bone fractures. In some instances, a bone plate surgical procedure may also be less difficult to perform in comparison to an intramedullary rod surgical procedure.

In any event, both intramedullary rods and bone plates can be associated with many risks, including, but not limited to breaking, bone screws that may loosen/pull-out over time, delayed healing/non-unions, infections, subsequent hardware removal issues (e.g., revision surgery) resulting in bone voids that can weaken the bone, etc.

Moreover, certain types of bone fractures may be subject to large tensile or traction forces that tend to "pull apart" a fractured bone, further complicating the bone healing process. Example bone fractures that can experience large tensile forces include, but are not limited to clavicle fractures, olecranon fractures, fibula fractures, patellar fractures, malleolar fractures, etc. In such cases, an intramedullary rod or bone plate alone may not provide an optimal solution for fixation strength and sustained fracture reduction during the bone healing process.

A tension band is another form of orthopedic internal fixation device that may be utilized to help resist tensile forces to increase fixation, reduce bone fractures, and help promote the bone healing process. However, a tension band alone may not provide optimal fixation strength, reduction characteristics, and/or bone healing in every scenario.

Accordingly, orthopedic fixation devices, systems, and methods that can provide improved fixation, reduction, and bone healing would be desirable.

SUMMARY

The various bone fixation devices, systems, and methods of the present disclosure have been developed in response to the present state of the art, and in particular, in response to the problems and needs in the art that have not yet been fully solved by currently available bone fixation devices, systems, and methods. In some embodiments, the bone fixation devices, systems, and methods of the present disclosure may provide improved fixation, reduction, and healing between bone fragments.

In some embodiments, a bone fixation assembly may include an elongate fixation member and a flexible tensioning element. The elongate fixation member may include a central longitudinal axis, a first portion couplable within a first intramedullary canal of a first bone fragment of a bone, a second portion couplable within a second intramedullary canal of a second bone fragment of the bone to provide fixation of the second bone fragment relative to the first bone fragment, a first transverse passageway formed through the first portion of the elongate fixation member, and a second transverse passageway formed through the second portion of the elongate fixation member. The flexible tensioning element may be couplable to the first and second portions of the elongate fixation member to secure the elongate fixation member to the bone. The first transverse passageway may be configured to receive the flexible tensioning element therethrough from a first direction transverse to the central longitudinal axis of the elongate fixation member, and the second transverse passageway may be configured to receive the flexible tensioning element therethrough from a second direction transverse to the central longitudinal axis of the elongate fixation member. The flexible tensioning element may be configured to span a bone fracture intermediate the first bone fragment and the second bone fragment to preload the bone fracture in compression to resist tensile force imparted across the bone fracture, thereby maintaining fixation of the first bone fragment relative to the second bone fragment.

In some embodiments of the bone fixation assembly, a first end of the flexible tensioning element may be couplable with a second end of the flexible tensioning element to secure the elongate fixation member to the bone.

In some embodiments of the bone fixation assembly, the flexible tensioning element may include a first tension band couplable to the first portion of the elongate fixation member through the first transverse passageway, and a second tension band couplable to the second portion of the elongate fixation member through the second transverse passageway.

In some embodiments of the bone fixation assembly, the first and second tension bands may be couplable to each other to secure the elongate fixation member to the bone.

In some embodiments of the bone fixation assembly, a first end of the first tension band may be couplable with a second end of the second tension band, and a second end of the first tension band may be couplable with a first end of the second tension band to form a crisscross pattern that spans the bone fracture and secures the elongate fixation member to the bone.

In some embodiments of the bone fixation assembly, a securing element may be couplable to the flexible tensioning element and configured to prevent loosening of the flexible tensioning element.

In some embodiments of the bone fixation assembly, a tensioner element may be couplable to the flexible tensioning element and configured to impart a tension force to the flexible tensioning element.

In some embodiments, a bone fixation assembly may include an elongate fixation member and a flexible tensioning element. The elongate fixation member may include a central longitudinal axis, a distal portion couplable to a first bone fragment of a bone, and a proximal portion couplable to a second bone fragment of the bone to provide fixation of the second bone fragment relative to the first bone fragment. The flexible tensioning element may be couplable to the proximal portion and the distal portion of the elongate fixation member to secure the elongate fixation member to the bone. The flexible tensioning element may be configured to span a bone fracture intermediate the first bone fragment and the second bone fragment to preload the bone fracture in compression to resist tensile force imparted across the bone fracture, thereby maintaining fixation of the first bone fragment relative to the second bone fragment.

In some embodiments of the bone fixation assembly, a first end of the flexible tensioning element may be couplable with a second end of the flexible tensioning element to secure the elongate fixation member to the bone.

In some embodiments of the bone fixation assembly, a surface of the elongate fixation member may include one or more channels configured to receive the flexible tensioning element therein to secure the elongate fixation member to the bone.

In some embodiments of the bone fixation assembly, the flexible tensioning element may include a first tension band couplable to the distal portion of the elongate fixation member, and a second tension band couplable to the proximal portion of the elongate fixation member and to the first tension band to secure the elongate fixation member to the bone.

In some embodiments of the bone fixation assembly, the elongate fixation member may include a first transverse passageway formed through the distal portion of the elongate fixation member. The first transverse passageway may be configured to receive the first tension band therethrough from a first direction transverse to the central longitudinal axis of the elongate fixation member. The elongate fixation member may also include a second transverse passageway formed through the proximal portion of the elongate fixation member. The second transverse passageway may be configured to receive the second tension band therethrough from a second direction transverse to the central longitudinal axis of the elongate fixation member.

In some embodiments of the bone fixation assembly, the elongate fixation member may include a longitudinal passageway configured to receive the flexible tensioning element therethrough.

In some embodiments of the bone fixation assembly, a securing element may be couplable to the flexible tensioning element and configured to prevent loosening of the flexible tensioning element.

In some embodiments of the bone fixation assembly, a tensioner element may be couplable to the flexible tensioning element and configured to impart a tension force to the flexible tensioning element.

In some embodiments, a method of fixing a first bone fragment of a bone relative to a second bone fragment of the bone may include forming one or more first bone tunnels in the first bone fragment and forming one or more second bone tunnels in the second bone fragment. The method may also include coupling a first portion of an elongate fixation member to the first bone fragment and coupling a second portion of the elongate fixation member to the second bone fragment to provide fixation of the second bone fragment relative to the first bone fragment. The method may additionally include passing a flexible tensioning element through the one or more first bone tunnels and the one or more second bone tunnels, coupling the flexible tensioning element to the first portion of the elongate fixation member and the second portion of the elongate fixation member to secure the elongate fixation member to the bone, and spanning a bone fracture intermediate the first bone fragment and the second bone fragment with the flexible tensioning element to preload the bone fracture in compression to resist tensile force imparted across the bone fracture, thereby maintaining fixation of the first bone fragment relative to the second bone fragment.

In some embodiments of the method, forming the one or more first bone tunnels in the first bone fragment may include at least one of: forming a first transverse bone tunnel in the first bone fragment, and forming a first longitudinal bone tunnel in a first intramedullary canal of the first bone fragment. Likewise, forming the one or more second bone tunnels in the second bone fragment comprises at least one of: forming a second transverse bone tunnel in the second bone fragment, and forming a second longitudinal bone tunnel in a second intramedullary canal of the second bone fragment.

In some embodiments of the method, coupling the first portion of the elongate fixation member to the first bone fragment may include coupling the first portion of the elongate fixation member within the first intramedullary canal of the first bone fragment. Likewise, coupling the second portion of the elongate fixation member to the second bone fragment may include coupling the second portion of the elongate fixation member within the second intramedullary canal of the second bone fragment.

In some embodiments of the method, coupling the first portion of the elongate fixation member to the first bone fragment may include coupling the first portion of the elongate fixation member to a first surface of the first bone fragment. Likewise, coupling the second portion of the elongate fixation member to the second bone fragment may include coupling the second portion of the elongate fixation member to a second surface of the second bone fragment.

In some embodiments, the method may also include coupling a first end of the flexible tensioning element with a second end of the flexible tensioning element to secure the elongate fixation member to the bone.

These and other features and advantages of the present disclosure will become more fully apparent from the following description and appended claims or may be learned by the practice of the devices, systems, methods, and instruments set forth hereinafter.

BRIEF DESCRIPTION OF THE DRAWINGS

Exemplary embodiments of the disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which.

Figure 1A:
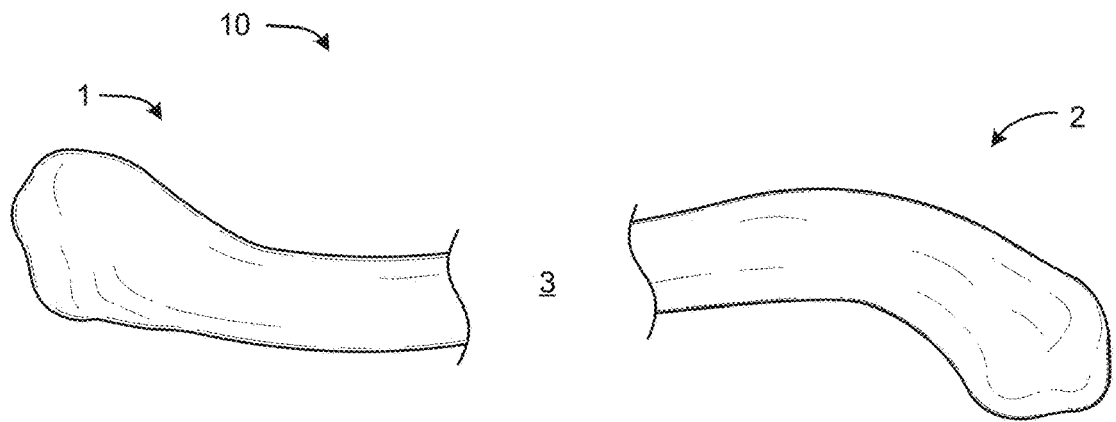
FIG. 1A illustrates a perspective side view of a fractured bone with first and second bone fragments, according to an example of the present disclosure.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The terms "coupled" and "couplable" can include components that are coupled to each other, or that are capable of being coupled to each other, via integral formation, as well as components that are removably and/or non-removably coupled/couplable with each other. Two components may be functionally coupled to each other even though they are not in direct contact with each other. The term "abutting" refers to components that may be in direct physical contact with each other, although the components may not necessarily be attached together.

As defined herein, the terms "flexible tensioning element" and "tension band" can comprise any tensioning element that may be utilized to preload a bone fracture in compression to resist tensile or distraction forces imparted across the bone fracture and maintain fixation/reduction of the bone fracture. Any flexible tensioning element or tension band described herein may include, but is not limited to a wire, a suture, a fabric, a strap, a strip, etc. Moreover, any flexible tensioning element or tension band described herein can comprise any flexible, semi-flexible, semi-rigid, or rigid material, or any combination thereof suitable for preloading a bone fracture in compression. Additionally, any flexible tensioning element or tension band described herein may include, but is not limited to a metal, an alloy, a plastic, a fiber (or group of fibers braided/woven together such as Dacron, etc.), a polymer, an elastomeric material, a flexible laminate, a resin, a film, an adhesive, etc.

Any of the devices, features, instruments, method steps, etc., that are described herein with respect to any particular bone fixation assembly or procedure may also be utilized in conjunction with (or omitted from) any other bone fixation assembly or that is described or contemplated herein in any combination.

FIGS. 1A-1L illustrate example devices, instruments, and method steps for a bone fixation assembly and procedure, according to an embodiment of the present disclosure.

FIG. 1 illustrates a bone 10 comprising a first bone fragment 1 and a second bone fragment 2 separated by a bone fracture 3. In some embodiments, the bone 10 may comprise a clavicle bone. However, it will be understood that the various devices, instruments, and method steps described herein can be utilized in any combination with each other and for any type of bone fracture including, but not limited to olecranon fractures, fibula fractures, patellar fractures, malleolar fractures, etc.

Figure 1B:
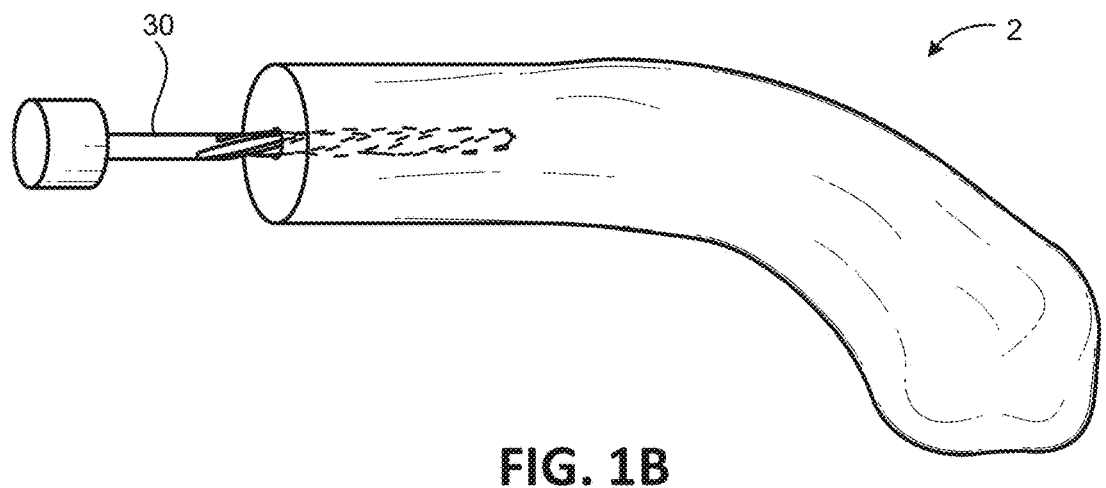
FIG. 1B illustrates a perspective side view of a reamer that may be utilized to prepare the intramedullary canals of the bone fragments of FIG. 1A.

FIG. 1B illustrates a first step of some embodiments of the procedure, in which the intramedullary canals of the first and second bone fragments 1, 2 may be prepared with a drill bit or reamer 30. The intramedullary canals of the first and second bone fragments 1, 2 may be drilled and/or reamed with any diameter drill bit or reamer to any desired depth within the intramedullary canal in order to form a prepared intramedullary canal. FIG. 1D illustrates the first and second bone fragments 1, 2 with prepared intramedullary canals including a first longitudinal bone tunnel or first intramedullary canal 11, and a second longitudinal bone tunnel or second intramedullary canal 12.

In some non-limiting embodiments of the procedure, a 4.2 mm diameter drill bit may be utilized and each intramedullary canal of the first and second bone fragments 1, 2 may be drilled and/or reamed to a depth of about 3 cm. However, it will be understood that in other embodiments any diameter size and/or any depth may be utilized, as desired.

Moreover, it will also be understood that in some embodiments of the procedure the intramedullary canals of the bone fragments may not require preparation, such as drilling, reaming, etc. For example, in some embodiments a suitable intramedullary rod may be press-fit and/or tamped into an unprepared intramedullary canal of a bone fragment.

Figure 1C:
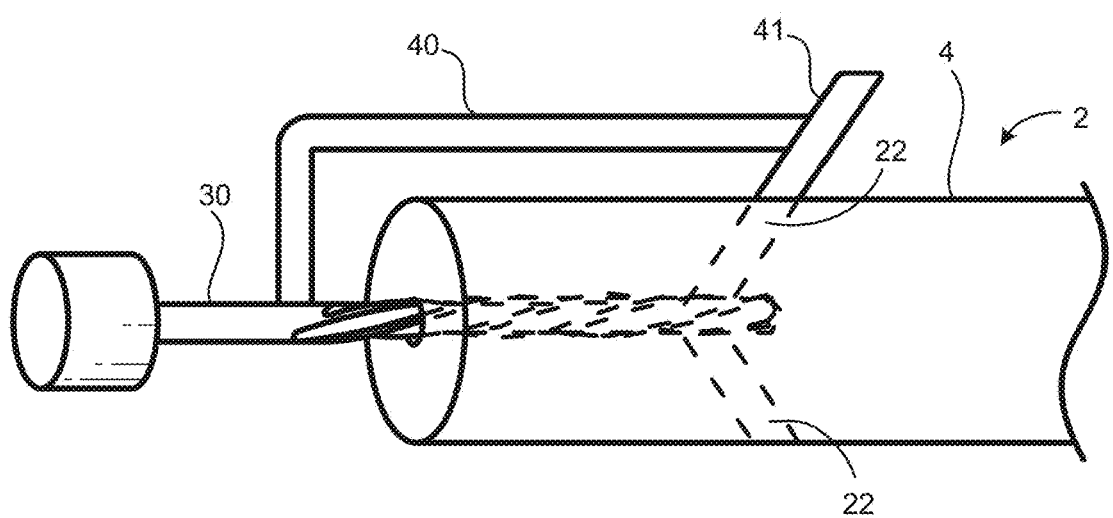
FIG. 1C illustrates a perspective side view of a drill guide that may be utilized to prepare one or more transverse bone tunnels in the bone fragments of FIG. 1A.
Figure 1D:
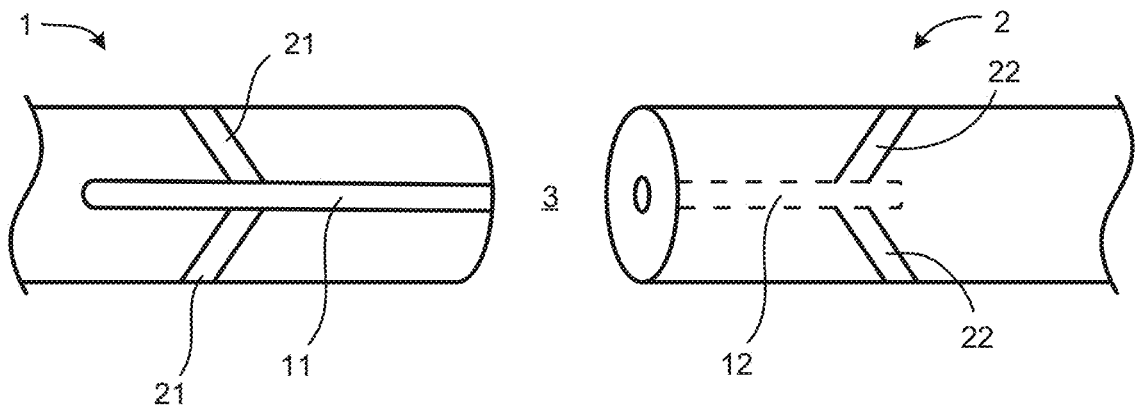
FIG. 1D illustrates a perspective side view of the bone fragments of FIG. 1A with prepared intramedullary canals and transverse bone tunnels.

FIG. 1C illustrates a second step of some embodiments of the procedure, in which a drill guide 40 may be utilized to place one or more transverse bone tunnels through a cortical surface 4 of the bone 10 and down into the prepared intramedullary canals of the bone fragments with a suitable drill bit (not shown).

In some embodiments, the drill guide 40 may be configured to utilize the reamer 30 as a reference to place a drill guide barrel 41 at a correct location along the cortical surface 4 of the bone 10, as shown in FIG. 1C. In this manner, the drill guide 40 may utilize the morphology and/or depth of the prepared intramedullary canals to guide the placement of the one or more transverse bone tunnels via the drill guide barrel 41. FIG. 1D illustrates the first and second bone fragments 1, 2 with prepared transverse bone tunnels including one or more first transverse bone tunnels 21 and one or more second transverse bone tunnels 22.

Figure 1E:
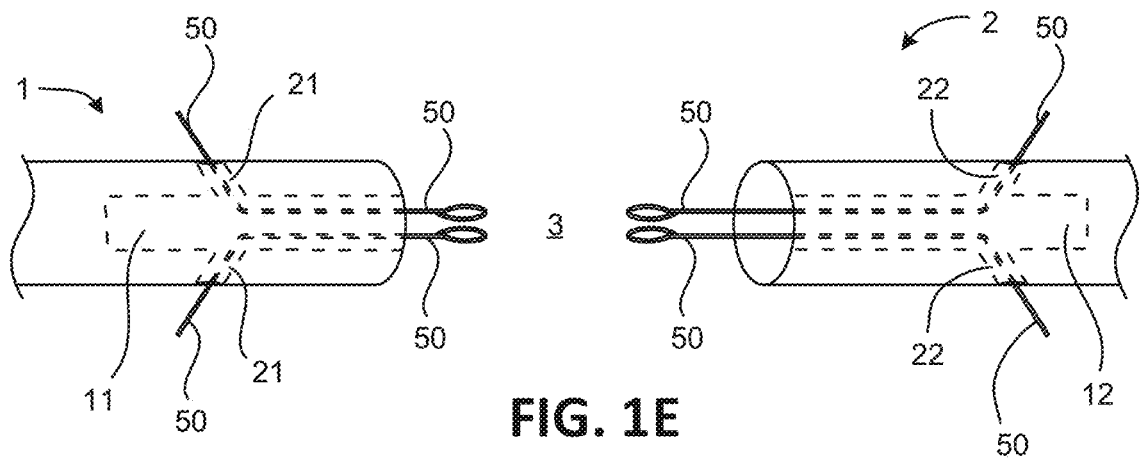
FIG. 1E illustrates a perspective side view of the bone fragments of FIG. 1A with retrieval wires inserted through the intramedullary canals and transverse bone tunnels.

FIG. 1E illustrates a third step of some embodiments of the procedure, in which one or more retrieval wires 50 may be placed through the first and second transverse bone tunnels 21, 22 and out the first and second intramedullary canals 11, 12. This step (and/or other similar steps described herein) may be facilitated with any suitable tool. In some embodiments, a magnetic wire retriever (not shown) with one or more magnets located on a tip of the magnetic wire retriever may be utilized. The magnetic wire retriever may be inserted into a bone tunnel to magnetically capture a wire and retrieve the wire from the bone tunnel. However, it will be understood that any other tool (or not tool at all) may be utilized to help facilitate the step of threading a flexible tensioning element through a bone tunnel.

Figure 1F:
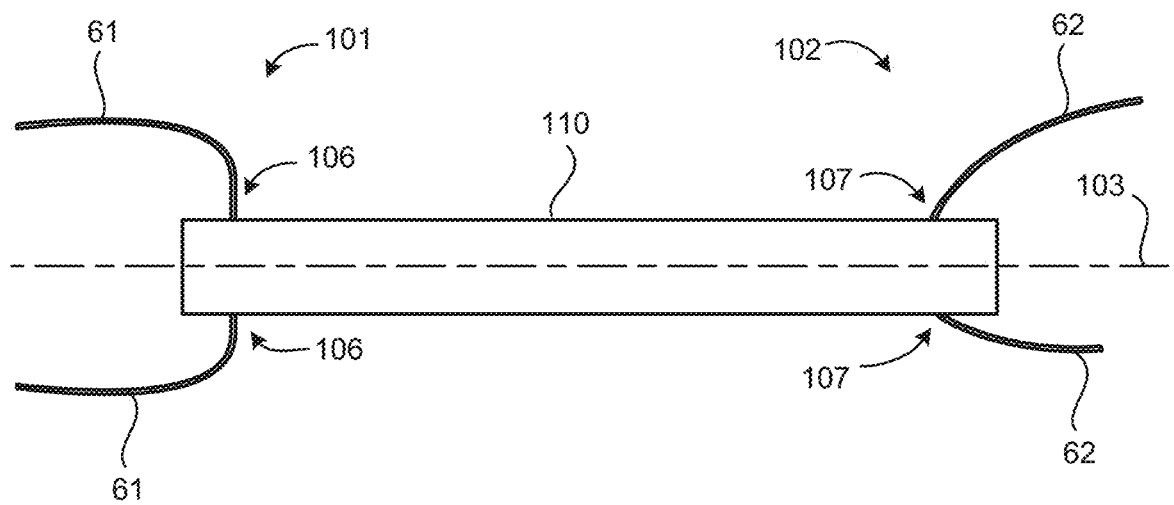
FIG. 1F illustrates a side view of an elongate fixation member with flexible tensioning elements passing through transverse passageways of the elongate fixation member, according to another embodiment of the present disclosure.

FIG. 1F illustrates an elongate fixation member 110, according to an embodiment of the present disclosure. The elongate fixation member 110 may generally include a distal portion or first portion 101, a proximal portion or second portion 102, and a central longitudinal axis 103.

In some embodiments, the elongate fixation member 110 may be configured to couple with at least one flexible tensioning element to secure the elongate fixation member to the bone 10.

In some embodiments, a first end of the flexible tensioning element may be couplable with a second end of the flexible tensioning element to secure the elongate fixation member 110 to the bone 10.

In some embodiments, the flexible tensioning element may comprise a first tension band or a first flexible tensioning element 61, as well as a second tension band or a second flexible tensioning element 62 in order to secure the elongate fixation member 110 to the bone 10.

In some embodiments, the elongate fixation member 110 may include a first transverse passageway 106 configured to receive the first flexible tensioning element 61 therethrough from a first direction transverse to the central longitudinal axis 103 of the elongate fixation member 110. The elongate fixation member 110 may also include a second transverse passageway 107 configured to receive the second flexible tensioning element 62 therethrough from a second direction transverse to the central longitudinal axis 103 of the elongate fixation member 110.

In some embodiments, the first direction and the second direction may be similar to each other.

In some embodiments, the first direction and the second direction may be opposite from each other.

In some embodiments, the first and second flexible tensioning elements 61, 62 may be couplable to each other in order to secure the elongate fixation member 110 to the bone 10.

Figure 1G:
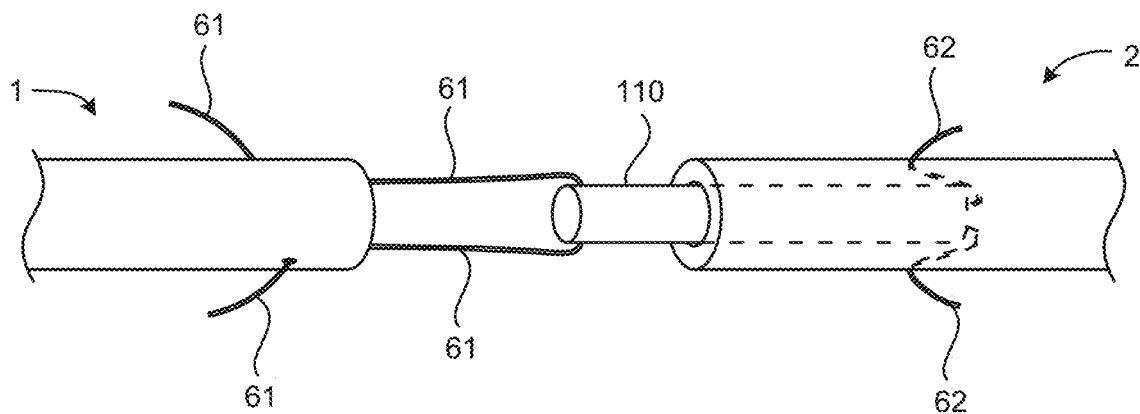
FIG. 1G illustrates a perspective side view of the elongate fixation member of FIG. 1F inserted into one of the prepared bone fragments of FIG. 1D with the flexible tensioning elements passing through the transverse bone tunnels.
Figure 1H:
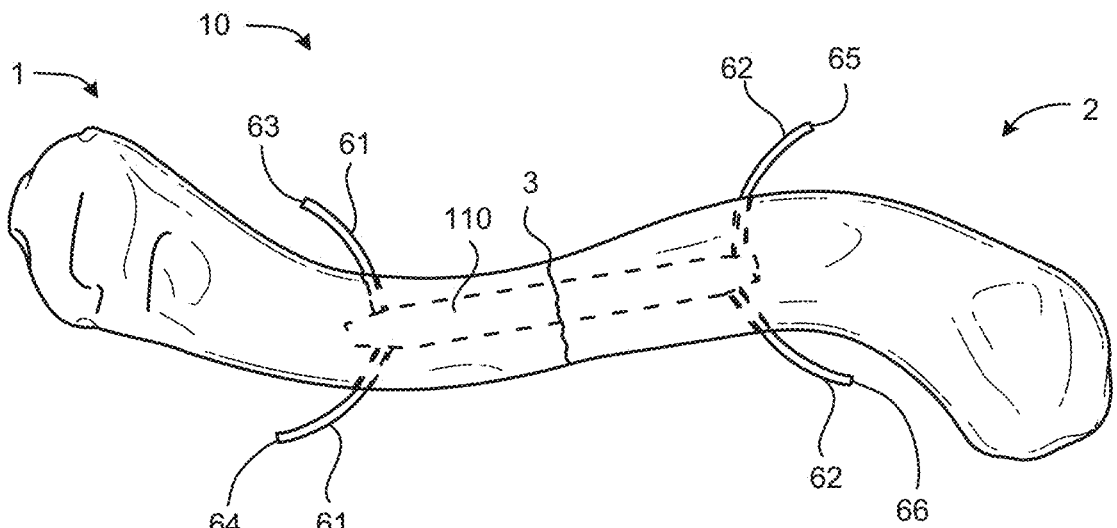
FIG. 1H illustrates a perspective side view of FIG. 1G with the elongate fixation member inserted into both bone fragments and the bone fracture reduced.
Figure 1I:
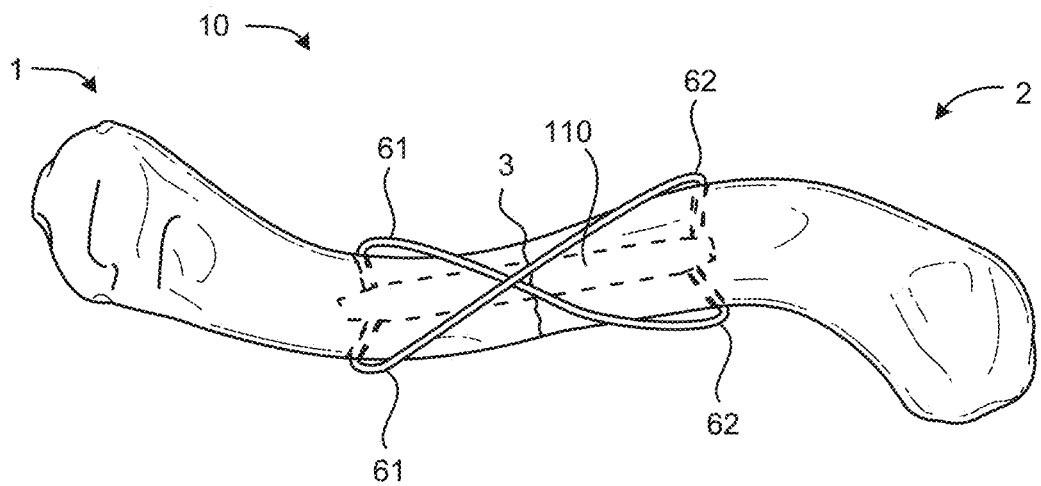
FIG. 1I illustrates a perspective side view of FIG. 1H with the flexible tensioning elements coupled to each other.

With reference to FIGS. 1H and 1I, in some embodiments a first end 63 of the first flexible tensioning element 61 may be couplable with a second end 66 of the second flexible tensioning element 62, and a second end 64 of the first flexible tensioning element 61 may be couplable with a first end 65 of the second flexible tensioning element 62 to form a crisscross pattern that spans the bone fracture 3 and secures the elongate fixation member 110 to the bone 10.

In some embodiments, the flexible tensioning elements may be configured to span the bone fracture 3 intermediate the first bone fragment 1 and the second bone fragment 2 to preload the bone fracture 3 in compression to resist tensile force imparted across the bone fracture 3, thereby maintaining fixation of the first bone fragment 1 relative to the second bone fragment 2.

In some embodiments, the elongate fixation member 110 may comprise an intramedullary rod.

In some embodiments, the elongate fixation member 110 may include a generally cylindrical shape.

In some embodiments, the elongate fixation member 110 may be solid or substantially solid. However, it will also be understood that in some embodiments the elongate fixation member 110 may comprise an at least partially hollow interior.

In some embodiments, the elongate fixation member 110 may comprise a rigid material to provide rigid fixation of the first and second bone fragments 1, 2 relative to each other.

FIG. 1G illustrates a fourth step of some embodiments of the procedure, in which the one or more retrieval wires 50 shown in FIG. 1E may be utilized to couple with and retrieve the first and second flexible tensioning elements 61, 62 in order to pull the first and second flexible tensioning elements 61, 62 through the intramedullary canals and back through the transverse bone tunnels formed in the bone fragments.

FIGS. 1G and 1H illustrate a fifth and sixth step of some embodiments of the procedure, in which the elongate fixation member 110 may be inserted into the prepared intramedullary canals of the first and second bone fragments 1, 2. Specifically, FIG. 1G illustrates the elongate fixation member 110 inserted into the second bone fragment 2 in a fifth step, and FIG. 1H illustrates the elongate fixation member 110 inserted into both the first and second bone fragments 1, 2 in a sixth step with the bone fracture 3 reduced.

Thus, in some embodiments the first portion 101 of the elongate fixation member 110 may be couplable within the first intramedullary canal 11 of the first bone fragment 1 of the bone 10, and the second portion 102 of the elongate fixation member 110 may be couplable within the second intramedullary canal 12 of the second bone fragment 2 of the bone 10 to provide fixation of the second bone fragment 2 relative to the first bone fragment 1.

In some embodiments, steps four through six discussed above can be performed together in a partial stepwise manner in order to ensure the flexible tensioning elements remain threaded through the transverse bone tunnels during the procedure. In this manner, initial reduction and/or initial fixation of the bone fracture 3 may be achieved through either or both of: (1) inserting the elongate fixation member 110 into the intramedullary canals of the bone fragments via a press fit; and/or (2) tensioning the flexible tensioning elements in order to draw the bone fragments together to achieve initial reduction and/or initial fixation of the bone fracture 3.

FIG. 1I illustrates a seventh step of some embodiments of the procedure, in which the first and second flexible tensioning elements 61, 62 may be woven around the bone fracture 3 and secured together. The first and second flexible tensioning elements 61, 62 may be configured to span the bone fracture 3 and preload the bone fracture 3 in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 110 with the first and second flexible tensioning elements 61, 62.

In some embodiments, the first and second flexible tensioning elements 61, 62 may be woven around the bone fracture 3 such that they form a crisscross pattern that spans the bone fracture 3 on a side of the bone 10.

In some embodiments, the first and second flexible tensioning elements 61, 62 may be woven around the bone fracture 3 such that they form a crisscross pattern that spans the bone fracture 3 on a superior side of the bone 10. However, it will also be understood that in other embodiments the flexible tensioning elements may be woven around the bone fracture 3 to form any suitable pattern and on any side of the bone 10 to achieve a desired resistance to tensile and/or distraction force that may be imparted across the bone fracture 3.

Figure 1J:
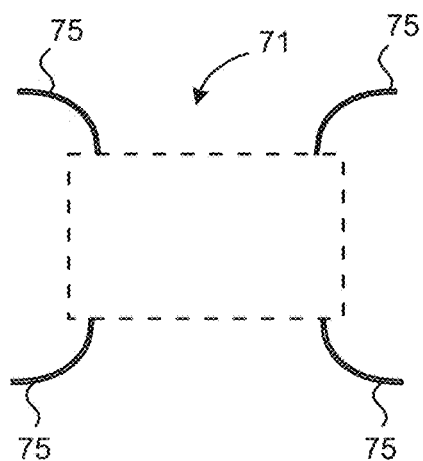
FIG. 1J illustrates a top view of a securing element, according to an embodiment of the present disclosure.
Figure 1K:
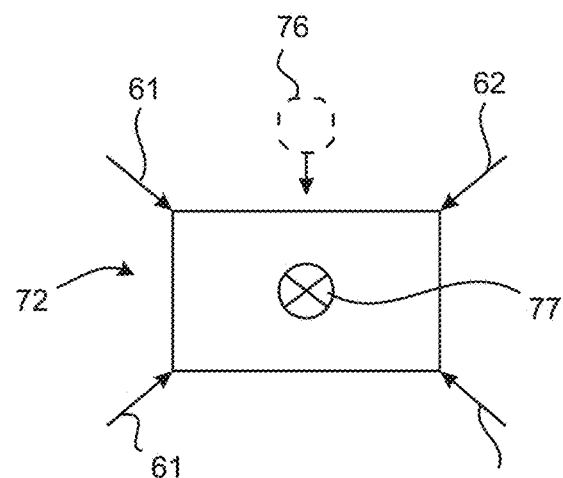
FIG. 1K illustrates a top view of a securing element, according to another embodiment of the present disclosure.
Figure 1L:
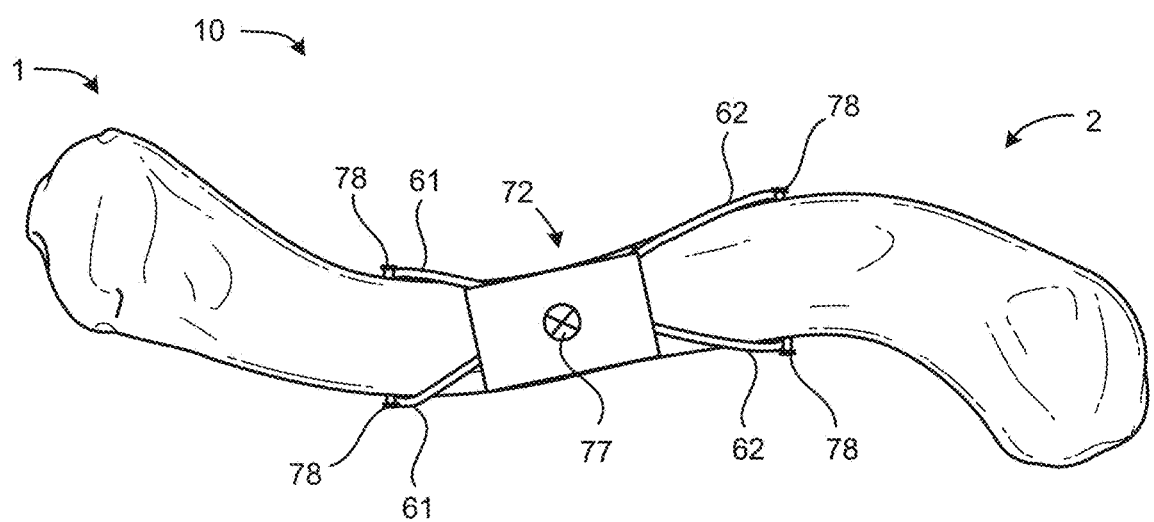
FIG. 1L illustrates a perspective side view of the securing element of FIG. 1K coupled to the flexible tensioning elements of FIG. 1J.

FIGS. 1J-1L illustrate an eighth step of some embodiments of the procedure, in which a clamp or securing element may be applied to the flexible tensioning elements to secure flexible tensioning elements in place and prevent the flexible tensioning elements from loosening over time.

FIG. 1J illustrates a top view of a first securing element 71, as one non-limiting example of the present disclosure, that may be utilized to secure the first and second flexible tensioning elements 61, 62 in place and prevent the first and second flexible tensioning elements 61, 62 from loosening over time. The first securing element 71 may include one or more attachment features 75 that may be configured to couple with the bone 10 and/or the first and second flexible tensioning elements 61, 62 to prevent loosening of the first and second flexible tensioning elements 61, 62 over time.

FIG. 1K illustrates a top view of a second securing element 72, as another non-limiting example of the present disclosure, that may be utilized to secure the first and second flexible tensioning elements 61, 62 in place and prevent the first and second flexible tensioning elements 61, 62 from loosening over time. FIG. 1L illustrates the second securing element 72 of FIG. 1K coupled to the first and second flexible tensioning elements 61, 62 of the bone fixation assembly from FIG. 1I.

In some embodiments, the second securing element 72 may be configured to receive and/or couple with the crisscross pattern formed by the first and second flexible tensioning elements 61, 62 to prevent the first and second flexible tensioning elements 61, 62 from loosening over time.

In some embodiments, the second securing element 72 may include one or more holes or channels (not shown) configured to receive the first and second flexible tensioning elements 61, 62 therein.

In some embodiments, the first and second flexible tensioning elements 61, 62 may be threaded into/through the second securing element 72 via the holes/channels in order to secure the flexible tensioning elements in place and prevent the flexible tensioning elements from loosening over time.

In some embodiments, the second securing element 72 may include a fastener 76 (e.g., such as a set screw, a screw cap, etc.) and a fastener aperture 77 configured to receive the fastener 76 therein. In these embodiments, the fastener 76 may removably couple with the second securing element 72 (e.g., via threading or by some other means) and may be configured to apply a compression force to the first and second flexible tensioning elements 61, 62 to prevent the first and second flexible tensioning elements 61, 62 from loosening over time.

In some embodiments, the fastener 76 may also be configured to apply a tension force to the first and second flexible tensioning elements 61, 62 in order to preload the bone fracture in compression to further resist tensile/distraction forces that may be imparted across the bone fracture 3 and provide additional fixation of the first bone fragment 1 relative to the second bone fragment 2. For example, the fastener 76 may include one or more prongs (not shown) that may engage with the first and second flexible tensioning elements 61, 62 as the fastener 76 rotates into the fastener aperture 77 via threading or by some other means. In this manner, the one or more prongs may also engage with and rotate the first and second flexible tensioning elements 61, 62 to tighten them up and impart a tension force to the first and second flexible tensioning elements 61, 62 to preload the bone fracture 3 in compression.

In some embodiments, the flexible tensioning elements may cross each other on top of the second securing element 72. However, it will also be understood that in other embodiments the flexible tensioning elements may cross each other within the second securing element 72 and/or under the second securing element 72.

In some embodiments, one or more bone fasteners 78 may also be utilized to provide additional tension and/or fixation to the first and second flexible tensioning elements 61, 62 in order to preload the bone fracture 3 in compression and/or to prevent the first and second flexible tensioning elements 61, 62 from loosening over time, as shown in FIG. 1L. In these embodiments, the one or more bone fasteners 78 may be configured to hold the ends of the first and second flexible tensioning elements 61, 62 in place with respect to the first and second bone fragments 1, 2.

In some embodiments, the one or more bone fasteners 78 may comprise bone screws configured to couple with the bone 10. The bone screws may include bone screw heads configured to capture and/or hold the first and second flexible tensioning elements 61, 62 in order to preload the bone fracture 3 in compression and/or to prevent the first and second flexible tensioning elements 61, 62 from loosening over time.

FIGS. 2A-2F illustrate example devices, instruments, and method steps for a bone fixation assembly and procedure, according to another embodiment of the present disclosure.

In some embodiments the bone 10 may comprise a distal or proximal end of a bone, such as a fractured olecranon process of the ulna, as one non-limiting example. However, it will be understood that the various devices, instruments, and method steps described herein can be utilized in any combination with each other and for any type of bone fracture including, but not limited to clavicle fractures, fibula fractures, patellar fractures, malleolar fractures, olecranon process fractures, etc.

Figure 2A:
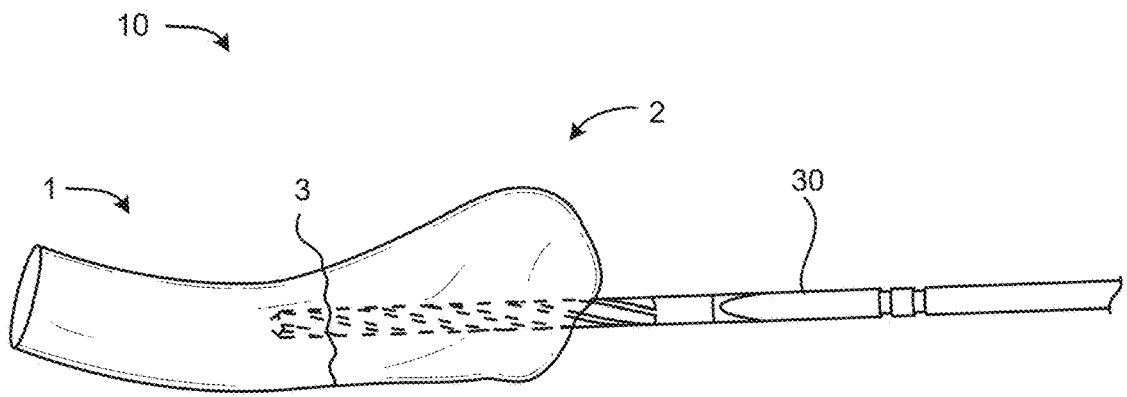
FIG. 2A illustrates a perspective side view of a fractured bone and reamer, according to another example of the present disclosure.
Figure 2B:
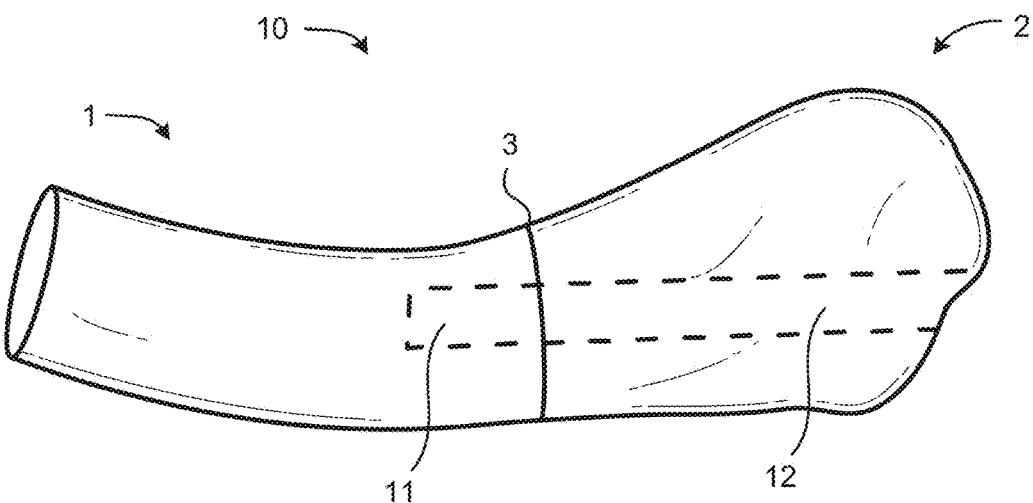
FIG. 2B illustrates a perspective side view of the bone of FIG. 2A with prepared intramedullary canals.

FIG. 2A illustrates a first step of some embodiments of the procedure, in which the intramedullary canals of the first and second bone fragments 1, 2 may be prepared with the reamer 30. The intramedullary canals of the first and second bone fragments 1, 2 may be drilled and/or reamed with any diameter drill bit or reamer to any desired depth within the intramedullary canals. FIG. 2B illustrates the first and second bone fragments 1, 2 with prepared first and second intramedullary canals 11, 12.

Figure 2C:
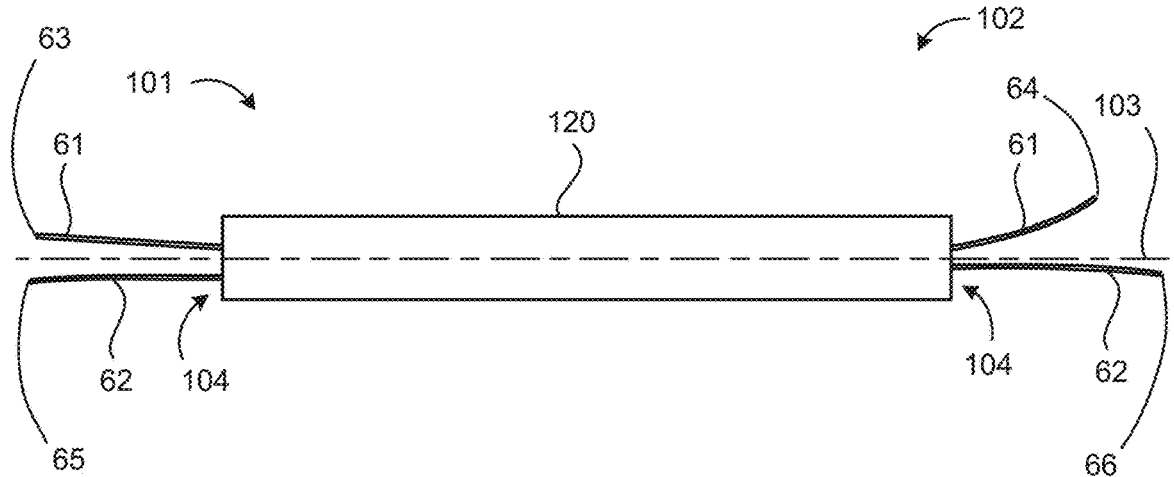
FIG. 2C illustrates a side view of an elongate fixation member with flexible tensioning elements passing through a longitudinal passageway of the elongate fixation member, according to an embodiment of the present disclosure.

FIG. 2C illustrates a side view of an elongate fixation member 120, according to another embodiment of the present disclosure. The elongate fixation member 120 may generally include the distal or first portion 101, the proximal or second portion 102, and the central longitudinal axis 103.

In some embodiments, the elongate fixation member 120 may be configured to couple with at least one flexible tensioning element to secure the elongate fixation member 120 to the bone 10.

In some embodiments, the elongate fixation member 120 may comprise a longitudinal passageway 104 formed through the elongate fixation member 120 and configured to receive the at least one flexible tensioning element therethrough.

In some embodiments, a first end of the at least one flexible tensioning element may be couplable with a second end of the at least one flexible tensioning element to secure the elongate fixation member 110 to the bone 10.

In some embodiments, the at least one flexible tensioning element may comprise the first flexible tensioning element 61 and the second flexible tensioning element 62 to secure the elongate fixation member 110 to the bone 10.

In some embodiments, the first and second flexible tensioning elements 61, 62 may be couplable to each other in order to secure the elongate fixation member 110 to the bone 10.

Figure 2D:
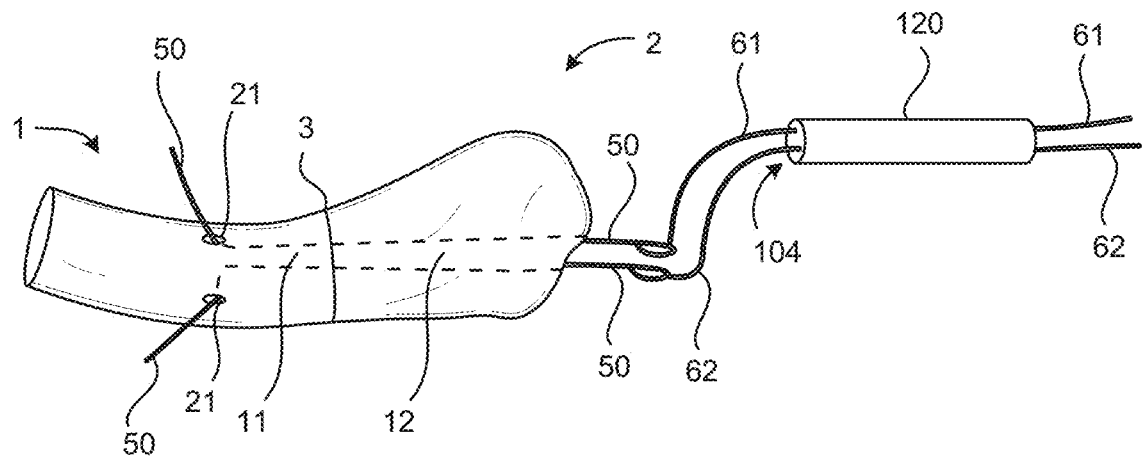
FIG. 2D illustrates a perspective side view of the bone of FIG. 2B with retrieval wires passing through transverse bone tunnels and the prepared intramedullary canals to retrieve flexible tensioning elements passing through the elongate fixation member of FIG. 2C.
Figure 2E:
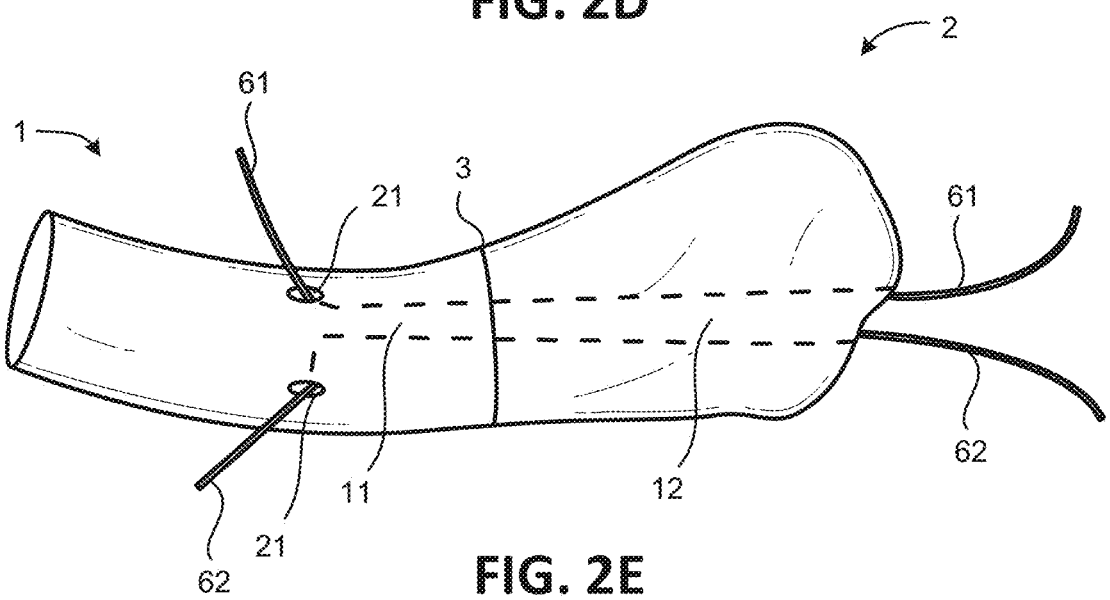
FIG. 2E illustrates a perspective side view of the bone of FIG. 2D with the flexible tensioning elements pulled through the transverse bone tunnels.
Figure 2F:
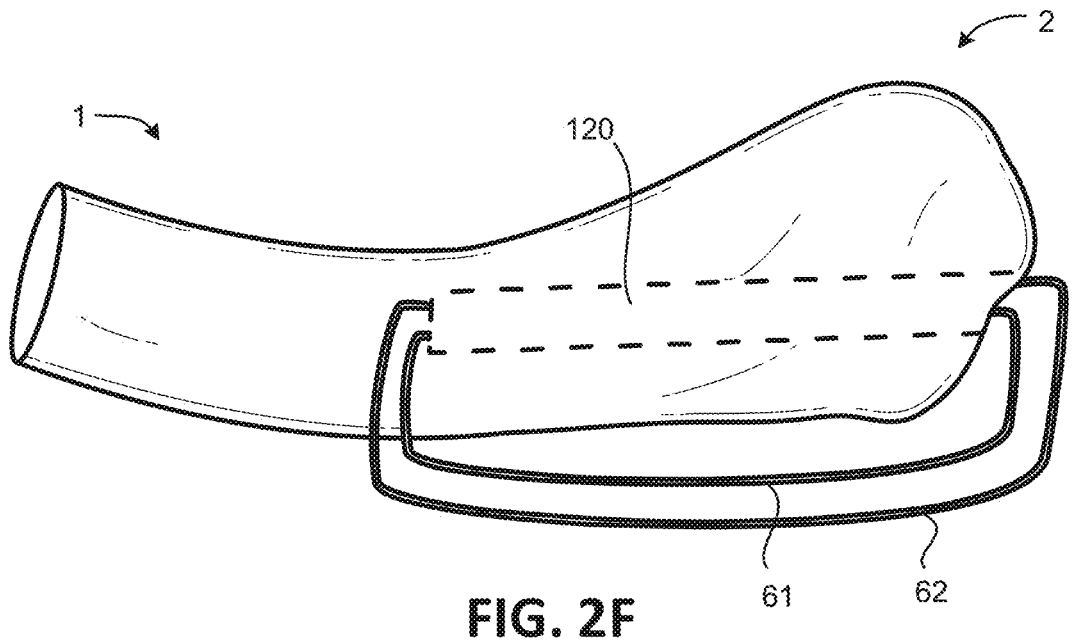
FIG. 2F illustrates a perspective side view of the bone of FIG. 2E with the elongate fixation member inserted into the prepared intramedullary canal and the flexible tensioning elements coupled to each other.

In some embodiments, the first end 63 of the first flexible tensioning element 61 may be couplable with the second end 64 of the first flexible tensioning element 61, and the first end 65 of the second flexible tensioning element 62 may be couplable with the second end 66 of the second flexible tensioning element 62 such that the first and second flexible tensioning elements 61, 62 span the bone fracture 3 and secure the elongate fixation member 120 to the bone 10, as shown in FIG. 2F.

In a second step of some embodiments of the procedure, one or more first transverse bone tunnels 21 may be formed in the first bone fragment 1, as can be seen in FIG. 2D. The one or more first transverse bone tunnels 21 may intersect the first intramedullary canal 11, as previously described herein. In some embodiments, one or more second transverse bone tunnels (not shown) may also be formed in the second bone fragment 2 that may intersect the second intramedullary canal 12. The one or more second transverse bone tunnels may be slightly spread apart from each other in the tip of the fractured olecranon process on either side of the second intramedullary canal 12. This will create more distance between the first and second flexible tensioning elements 61, 62 which can provide more rotational control of the fracture and/or allow the first and second flexible tensioning elements 61, 62 to be buried underneath soft tissues with a lower profile to avoid prominent and/or painful protrusion of the first and second flexible tensioning elements 61, 62 (e.g., under the skin, muscles, soft tissues, etc.).

FIG. 2D illustrates a third step of some embodiments of the procedure, in which one or more retrieval wires 50 may be placed through the first transverse bone tunnels 21 and the first and second intramedullary canals 11, 12 to retrieve the first and second flexible tensioning elements 61, 62, as previously described herein. FIG. 2E shows the first and second flexible tensioning elements 61, 62 pulled through the first transverse bone tunnels 21.

FIG. 2F illustrates a fourth step of some embodiments of the procedure, in which the elongate fixation member 120 may be inserted into the prepared first and second intramedullary canals 11, 12 of the first and second bone fragments 1, 2.

FIG. 2F also illustrates a fifth step of some embodiments of the procedure, in which the first and second flexible tensioning elements 61, 62 may be coupled to each other, woven around the bone fracture 3, and secured together.

In some embodiments, the first and second flexible tensioning elements 61, 62 may be additionally secured in place and/or tensioned via any of the securing element and/or tensioning element designs described or contemplated herein.

Thus, the first and second flexible tensioning elements 61, 62 may be configured to span the bone fracture 3 and preload the bone fracture in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 120 with the first and second flexible tensioning elements 61, 62.

As previously discussed, the devices and procedures described herein can be utilized for bone fractures in other various locations throughout the body. For example, the procedure for an olecranon process fracture could be slightly modified for a different type of bone fracture, such as a fractured fibula. In this example, the technique would be similar to the olecranon process, except the surgeon would drill up initially from the tip of the fibula along the lateral ankle, then drill holes past the fracture into the fibulae shaft proximal to the fracture. Then, the surgeon would pull the device from the tip of the lateral malleolus, through the fracture site, and then secure the flexible tensioning element as previously discussed.

Figure 3A:
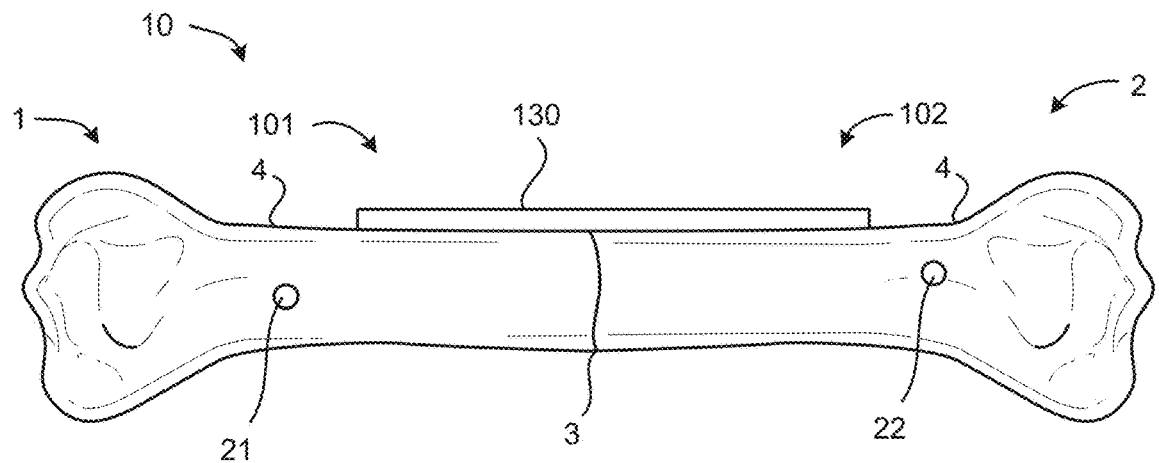
FIG. 3A illustrates a side view of a fractured bone coupled to a bone plate, according to another example of the present disclosure.
Figure 3B:
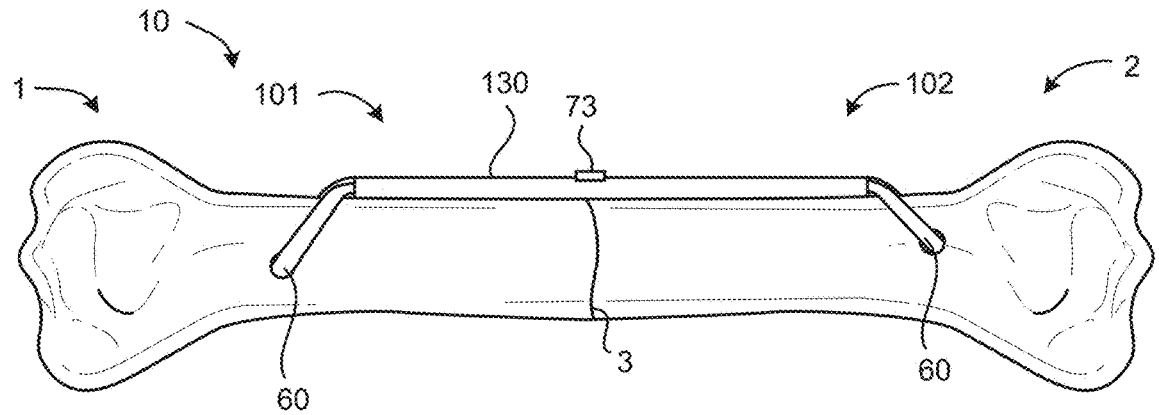
FIG. 3B illustrates a side view of the fractured bone of FIG. 3A including a flexible tensioning element coupled to the bone plate.
Figure 3C:
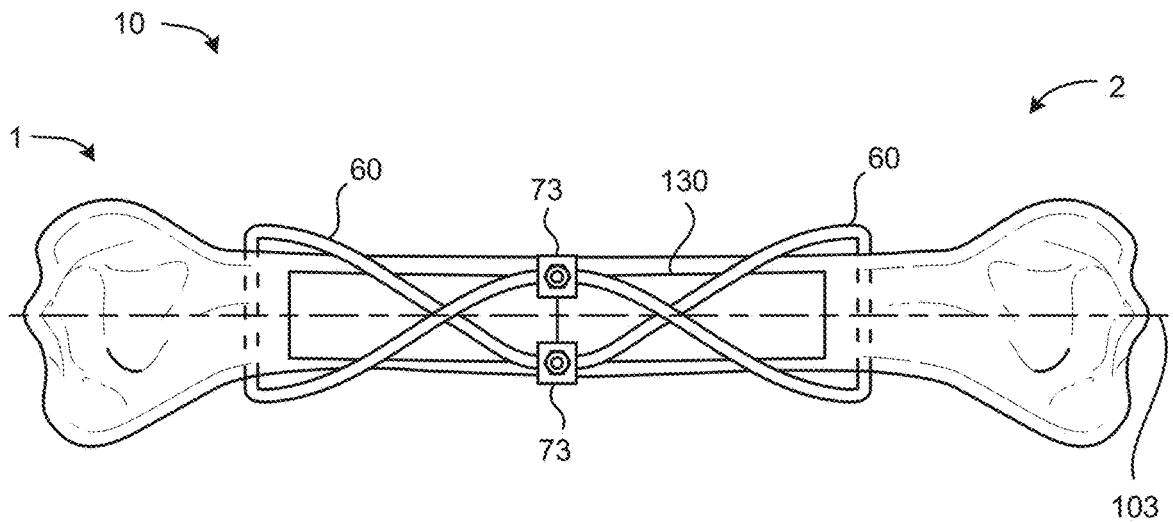
FIG. 3C illustrates a top view of fractured bone of FIG. 3B.

FIGS. 3A-3C illustrate an example bone fixation assembly and procedure that utilizes an elongate fixation member 130 comprising a bone plate in combination with a flexible tensioning element 60, according to another embodiment of the present disclosure.

In some embodiments, the bone fracture 3 may be provisionally reduced and the elongate fixation member 130 may be secured to cortical surfaces 4 of the first and second bone fragments 1, 2 (e.g., via bone screws, not shown) in order to provide initial fixation for the bone fracture 3. In some embodiments, the elongate fixation member 130 may be located superiorly on the bone 10. However, in other embodiments the elongate fixation member 130 may be placed along any side of the bone 10, and/or multiple bone plates may be utilized to stabilize the bone fracture 3 on any side of the bone 10.

In some embodiments, first and second transverse bone tunnels 21, 22 may be drilled through the first and second bone fragments 1, 2. In some embodiments, the first and second transverse bone tunnels 21, 22 may be drilled through the first and second bone fragments 1, 2 in an anterior to posterior direction (e.g., for a clavicle bone). In some embodiments, the first and second transverse bone tunnels 21, 22 may be drilled through the first and second bone fragments 1, 2 at locations that are past the proximal and distal portions 101, 102 of the elongate fixation member 130. However, it will be understood that in other embodiments the first and second transverse bone tunnels 21, 22 may not be drilled through the first and second bone fragments 1, 2 in any particular direction, or at any location past the proximal and distal portions 101, 102 of the elongate fixation member 130.

In some embodiments, the flexible tensioning element 60 may be threaded through the first and second transverse bone tunnels 21, 22 and woven around or cinched over the bone fracture 3 such that the flexible tensioning element 60 forms one or more crisscross patterns on top of, within, and/or below the elongate fixation member 130. However, it will also be understood that in other embodiments the flexible tensioning element 60 may be woven around the bone fracture 3 to form any suitable pattern on any side of the bone 10 and/or any side of the elongate fixation member 130 to preload the bone fracture 3 in compression and resist tensile/distraction forces imparted across the bone fracture 3.

In some embodiments, the flexible tensioning element 60 may comprise a single flexible tensioning element.

In some embodiments, the flexible tensioning element 60 may comprise one or more flexible tensioning elements that may be couplable to each other, such as the first and second flexible tensioning elements 61, 62 previously described herein.

In some embodiments, the elongate fixation member 130 may comprise one or more grooves (not shown) located on top of, within, or on the bottom of the elongate fixation member 130 that may be configured to receive the flexible tensioning element 60 therein to achieve a lower overall profile and reduce the risk of prominence and/or complications due to soft tissue disturbances.

In some embodiments, the flexible tensioning element 60 may be threaded through one or more sleeves (not shown) to prevent the flexible tensioning element 60 from cutting through the bone 10 over time. The one or more sleeves may be made of any biocompatible material including, but not limited to metals, plastics, PEEK, rubber, silicone, etc.

In some embodiments, the flexible tensioning element 60 may also be secured in place and/or tensioned via one or more third securing elements 73 (see FIG. 3C), which may include any of the securing element designs and/or tensioning element designs described or contemplated herein.

Figure 4A:
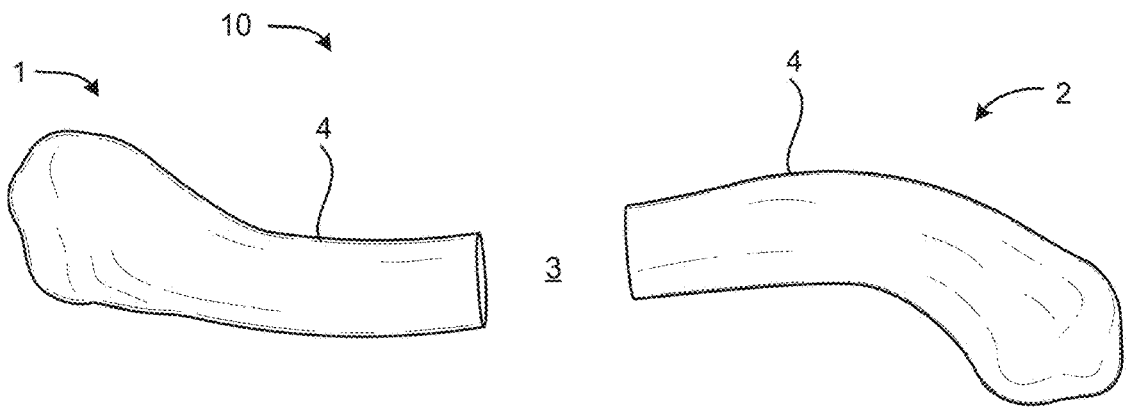
FIG. 4A illustrates a perspective side view of a fractured bone with first and second bone fragments, according to an example of the present disclosure.
Figure 4B:
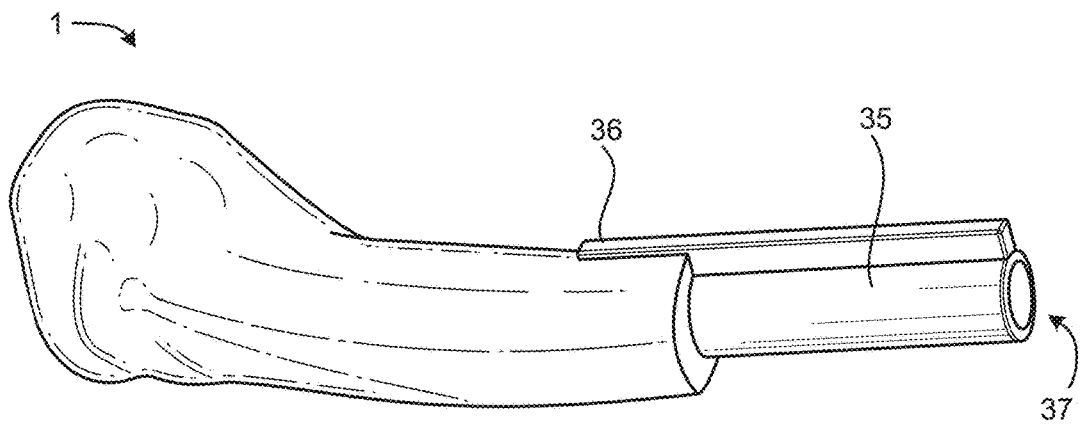
FIG. 4B illustrates a perspective side view of a reamer guide that may be utilized with the bone fragments of FIG. 4A.
Figure 4C:
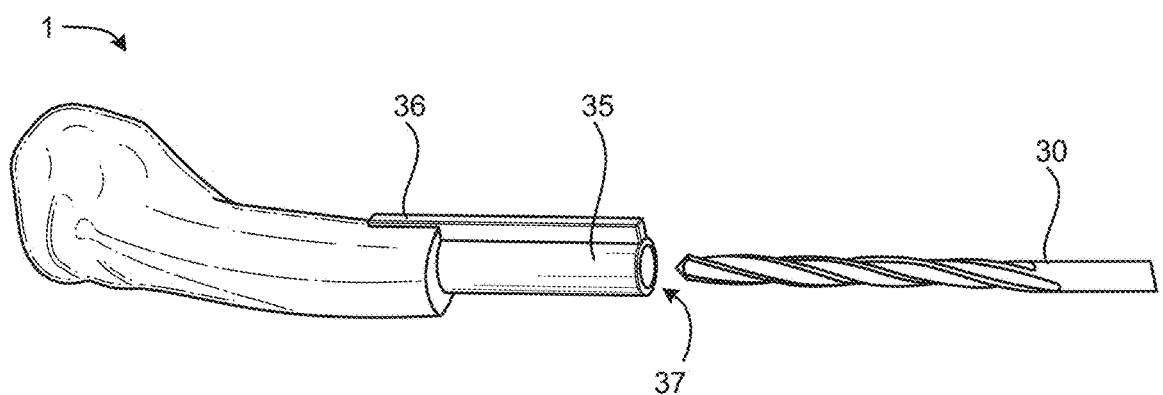
FIG. 4C illustrates a perspective side view of a reamer that may be utilized to prepare the intramedullary canals of the bone fragments of FIG. 4A.
Figure 4D:
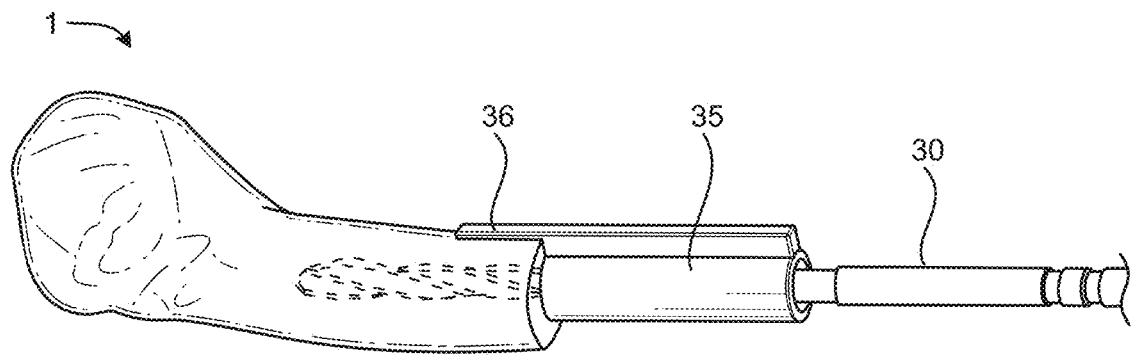
FIG. 4D illustrates a perspective side view of the reamer and reamer guide preparing the intramedullary canal of the first bone fragment of FIG. 4A.
Figure 4E:
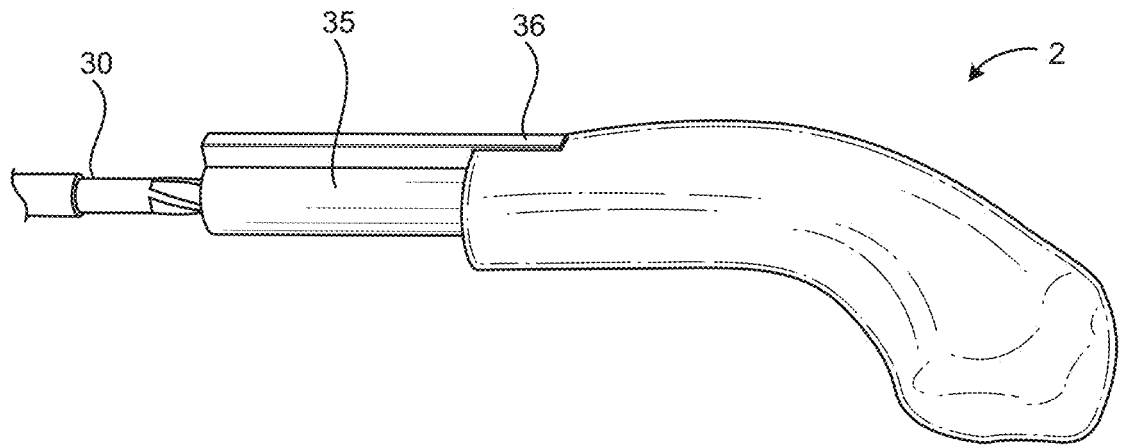
FIG. 4E illustrates a perspective side view of the reamer and reamer guide preparing the intramedullary canal of the second bone fragment of FIG. 4A.
Figure 4F:
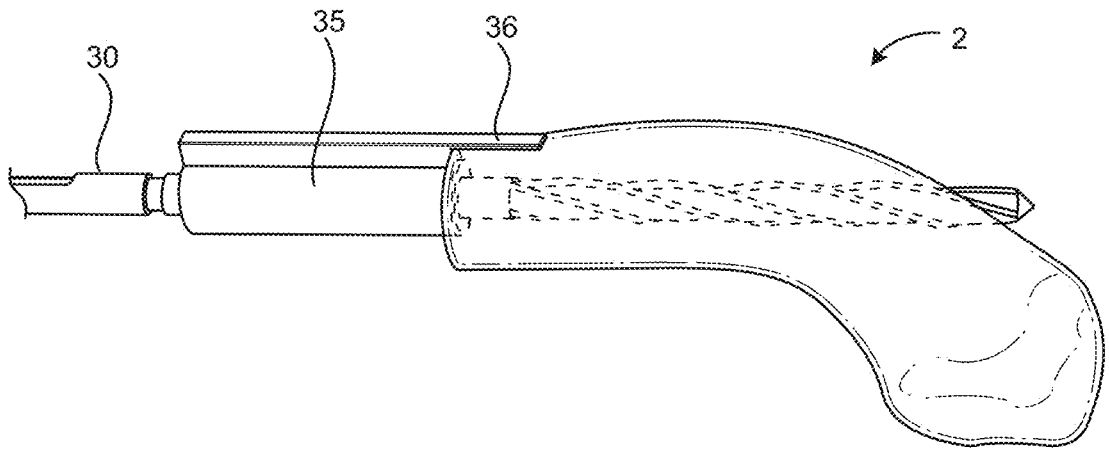
FIG. 4F illustrates another perspective side view of the reamer and reamer guide preparing the intramedullary canal of the second bone fragment of FIG. 4A.
Figure 4G:
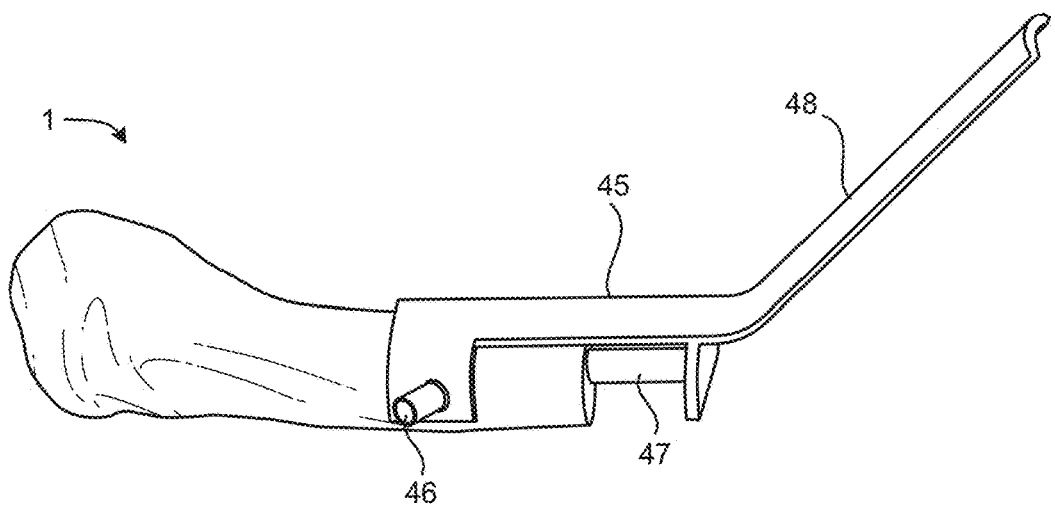
FIG. 4G illustrates a perspective side view of a drill guide that may be utilized to prepare transverse bone tunnels through the bone fragments of FIG. 4A.
Figure 4H:
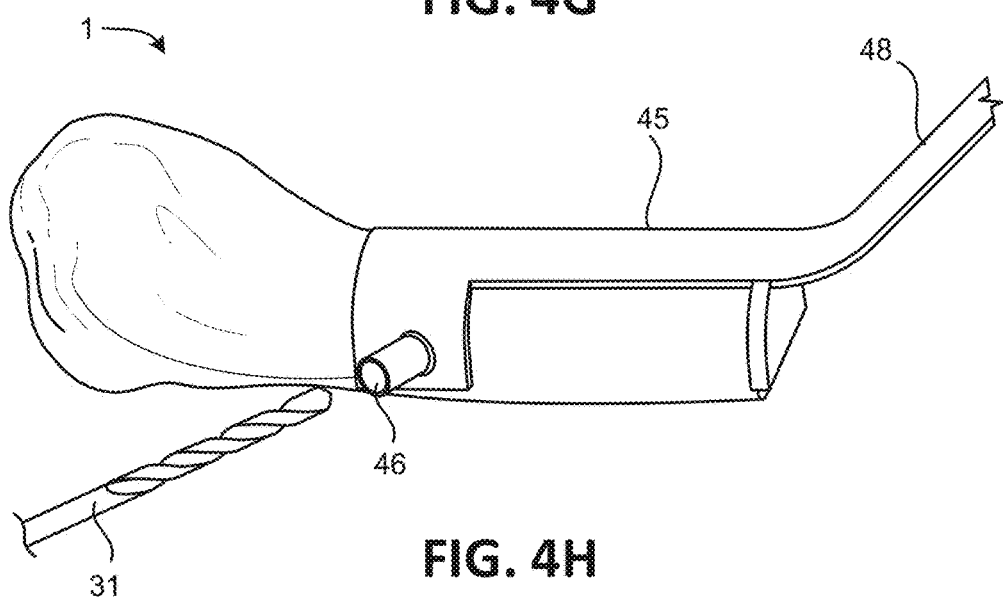
FIG. 4H illustrates a perspective side view of a drill bit that may be utilized to prepare the transverse bone tunnels through the bone fragments of FIG. 4A.
Figure 4I:
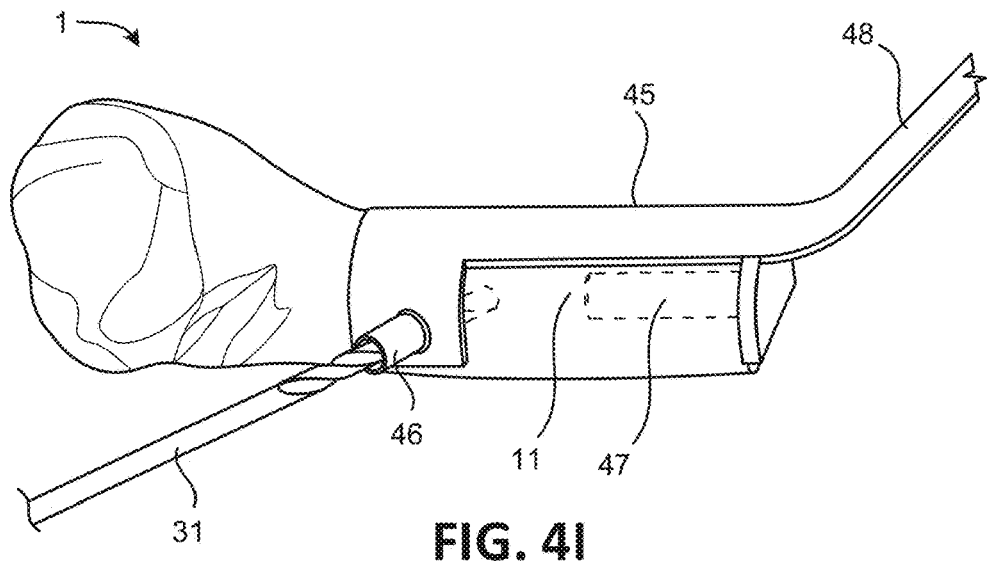
FIG. 4I illustrates a perspective side view of the drill guide and the drill bit preparing the transverse bone tunnels through the bone fragments of FIG. 4A.
Figure 4J:
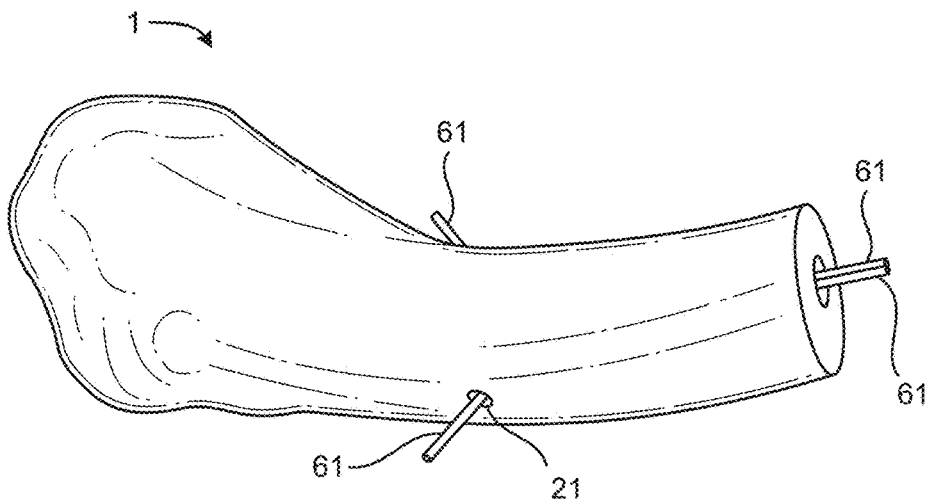
FIG. 4J illustrates a perspective side view of a prepared first bone fragment with flexible tensioning elements passing therethrough.
Figure 4K:
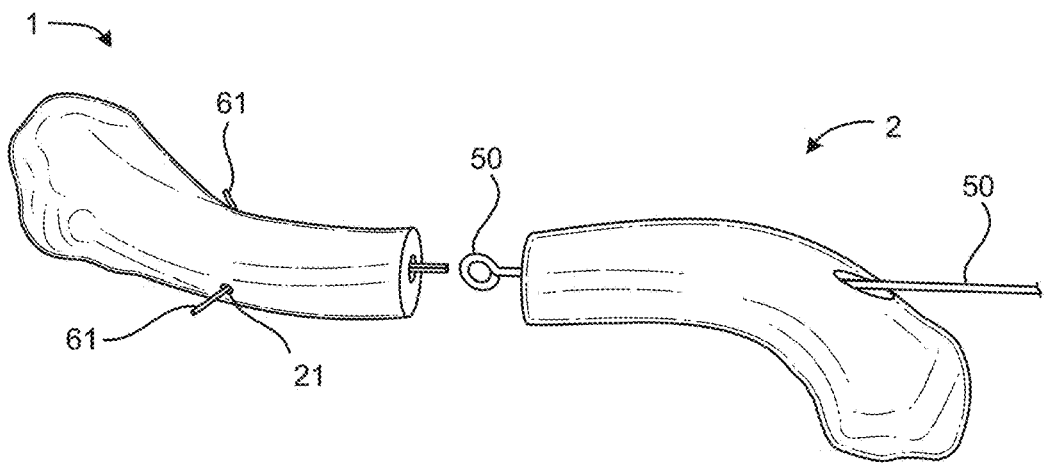
FIG. 4K illustrates a perspective side view of the prepared first bone fragment shown in FIG. 4J and a prepared second bone fragment with a retrieval wire passing therethrough.
Figure 4L:
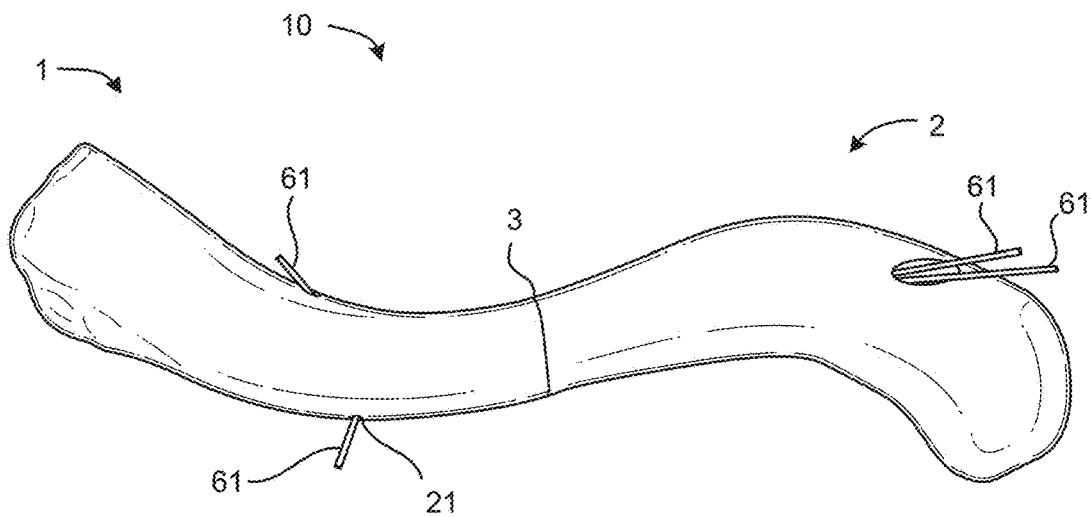
FIG. 4L illustrates a perspective side view of the bone fragments of FIG. 4K with flexible tensioning elements passing therethrough.
Figure 4M:
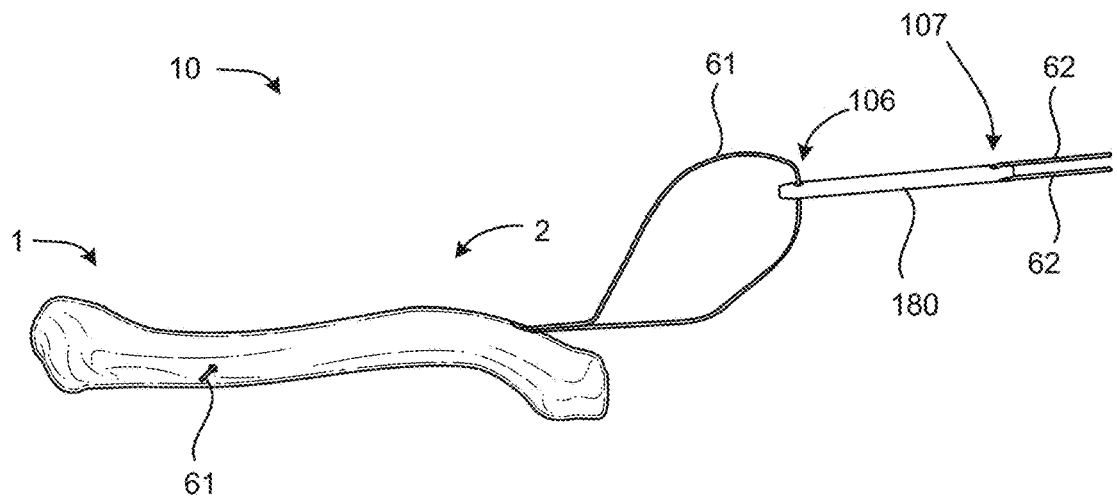
FIG. 4M illustrates a perspective side view of FIG. 4L with the flexible tensioning elements coupled to an elongate fixation member, similar to that shown in FIG. 8E.
Figure 4N:
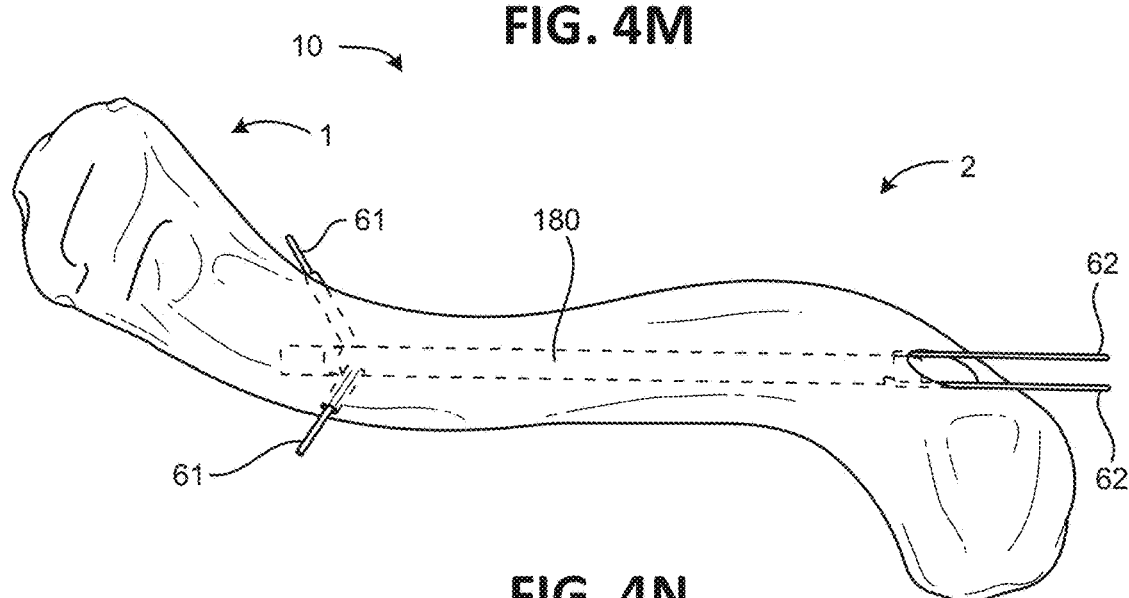
FIG. 4N illustrates a perspective side view of FIG. 4M with the elongate fixation member inserted into the intramedullary canals of the bone fragments.
Figure 4O:
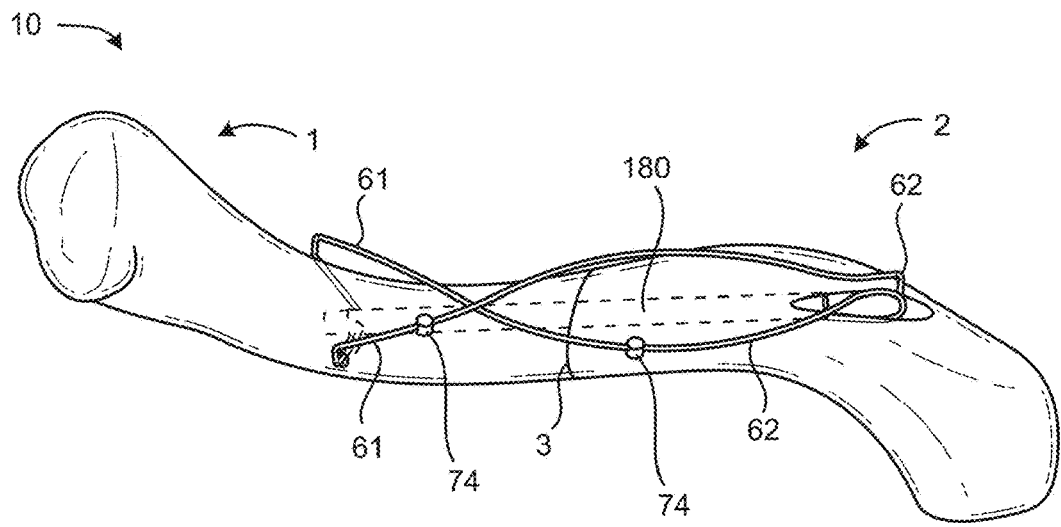
FIG. 4O illustrates a perspective side view of FIG. 4N with the flexible tensioning elements coupled to each other.

FIGS. 4A-4O illustrate example devices, instruments, and method steps for a bone fixation assembly and surgical procedure that may be performed from a lateral approach, according to another embodiment of the present disclosure.

In some embodiments, the bone 10 illustrated in FIG. 4A may comprise a clavicle bone. However, it will be understood that the various devices, instruments, and method steps described herein may be utilized in any combination with each other and for any type of bone fracture including, but not limited to olecranon fractures, fibula fractures, patellar fractures, malleolar fractures, etc.

FIG. 4B-4F illustrate a first step of some embodiments of the procedure, in which the first and second intramedullary canals 11, 12 of the first and second bone fragments 1, 2 may be prepared with a drill bit or reamer 30.

In some embodiments, the reamer 30 may be guided through a reamer passageway 37 that is formed through a reamer guide 35.

In some embodiments, the reamer guide 35 may also include a reference member 36 projecting from the reamer guide 35.

In some embodiments, the reference member 36 may be configured to abut a cortical surface 4 of the first and/or second bone fragments 1, 2 to orient the reamer passageway 37 with respect to the cortical surfaces 4 of the first and/or second bone fragments 1, 2.

As previously discussed, the first and second intramedullary canals 11, 12 of the first and second bone fragments 1, 2 may be drilled and/or reamed with any diameter drill bit or reamer to any desired depth within the intramedullary canal in order to form prepared intramedullary canals. Moreover, it will also be understood that in some embodiments of the procedure the intramedullary canals of the bone fragments may not require preparation, such as drilling, reaming, etc. For example, in some embodiments a suitable elongate fixation member may be press-fit and/or tamped into an unprepared intramedullary canal of a bone fragment.

FIGS. 4G-4I illustrate a second step of some embodiments of the procedure, in which a drill guide 45 and drill bit 31 may be utilized to place one or more first transverse bone tunnels 21 through the cortical surface 4 of the first bone fragment 1 down into the prepared first intramedullary canal 11.

In some embodiments, the drill guide 45 may include one or more drill guide barrels 46, an insert member 47, and a handle 48.

In some embodiments, the insert member 47 may be inserted into the prepared first intramedullary canal 11 to orient the one or more drill guide barrels 46 with respect to the prepared first intramedullary canal 11 of the first bone fragment 1.

FIGS. 4J-4L illustrate a third step of some embodiments of the procedure, in which a retrieval wire 50 may be placed through the second intramedullary canal 12 of the second bone fragment 2 in order to capture and pull the first flexible tensioning elements 61 through the second intramedullary canal 12 of the second bone fragment 2, as shown in FIG. 4L.

FIG. 4M illustrates a fourth step of some embodiments of the procedure, in which one of the first flexible tensioning elements 61 may be passed through the first transverse passageway 106 of the elongate fixation member 180 and then coupled to the other one of the first flexible tensioning elements 61, as can be seen in FIG. 4M. The elongate fixation member 180 will be discussed in more detail below with respect to FIG. 8E.

FIG. 4N illustrates a fifth step of some embodiments of the procedure, in which the elongate fixation member 180 may be inserted into the prepared first and second intramedullary canals 11, 12 of the first and second bone fragments 1, 2 from a lateral approach. This may be accomplished by pulling the first flexible tensioning elements 61 through the first transverse bone tunnels 21, and/or by impacting the distal end of the elongate fixation member 180 with an impact driver (not shown).

FIG. 4O illustrates a sixth step of some embodiments of the procedure, in which the first and second flexible tensioning elements 61, 62 may be woven around the bone fracture 3 and secured together, as previously described herein. The first and second flexible tensioning elements 61, 62 may be configured to span the bone fracture 3 and preload the bone fracture 3 in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 180 with the first and second flexible tensioning elements 61, 62.

In some embodiments, the first and second flexible tensioning elements 61, 62 may also be secured in place and/or tensioned via one or more fourth securing elements 74 (see FIG. 4O), which may include any of the securing element designs and/or tensioning element designs described or contemplated herein.

FIGS. 5A-5H illustrate example devices, instruments, and method steps for a bone fixation assembly and surgical procedure that may be performed from a lateral approach, according to another embodiment of the present disclosure.

In some embodiments, the first and second bone fragments 1, 2 may be prepared in a similar manner to the first bone fragment 1 shown in FIGS. 4A-4I in a first step and a second step. However, the first and second intramedullary canals 11, 12 of the first and second bone fragments 1, 2 may also be tapped with a tap tool 80 in a third step to form internal bone threads 81 within the first and second intramedullary canals 11, 12 (e.g., see FIG. 5A).

Figure 5A:
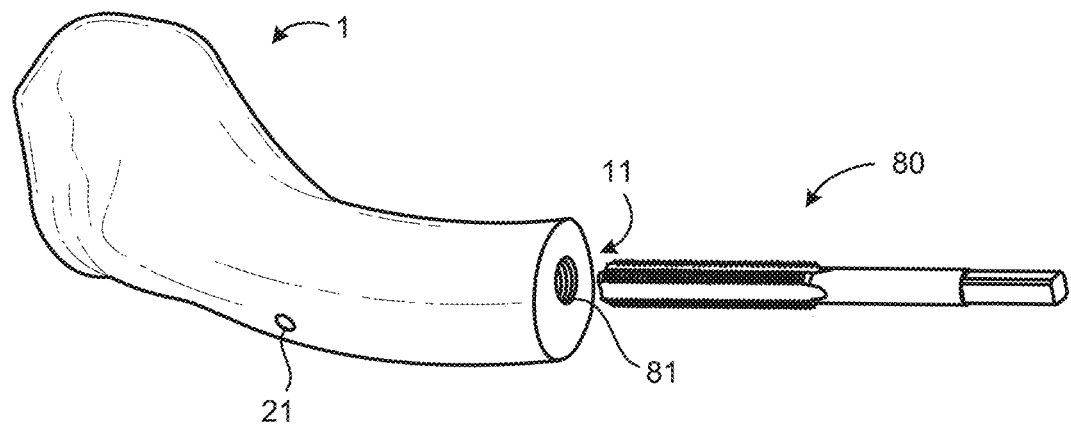
FIG. 5A illustrates a perspective side view of a tap that may be utilized to prepare a threaded intramedullary canal within the bone fragments of FIG. 4A, according to another example of the present disclosure.
Figure 5B:
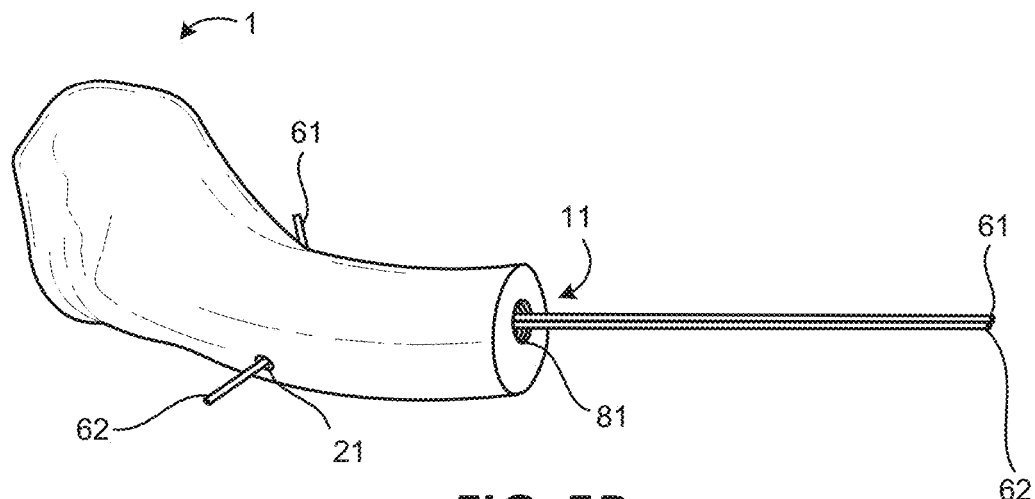
FIG. 5B illustrates a perspective side view of the prepared first bone fragment shown in FIG. 5A with flexible tensioning elements passing therethrough.
Figure 5C:
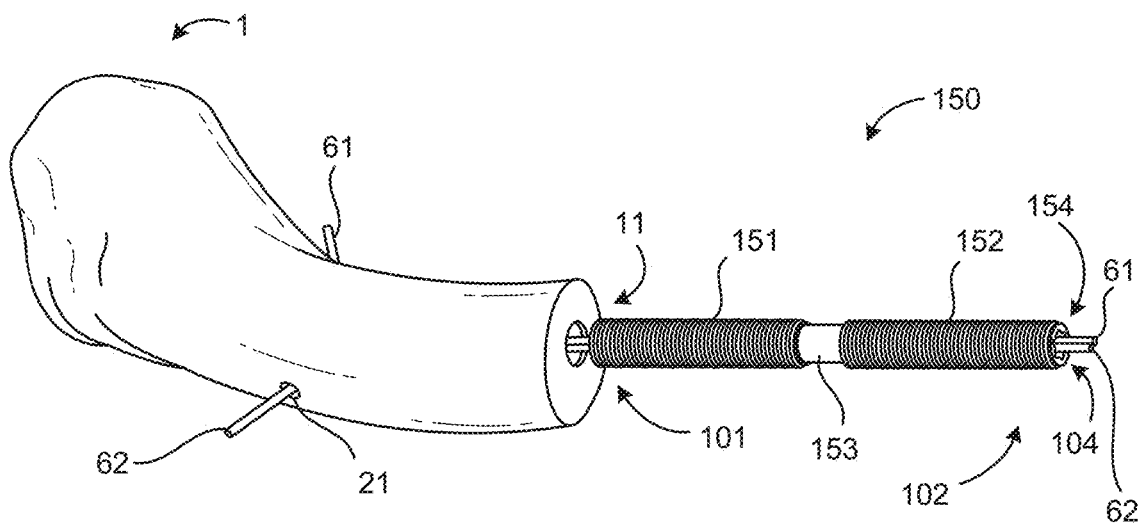
FIG. 5C illustrates a perspective side view of FIG. 5B with an elongate fixation member, according to another embodiment of the present disclosure.
Figure 5D:
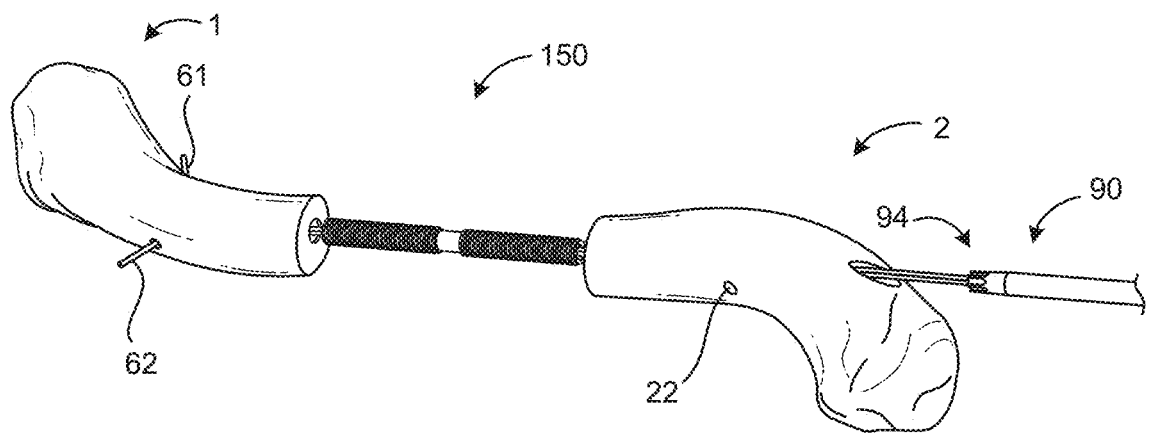
FIG. 5D illustrates a perspective side view of FIG. 5C with a prepared second bone fragment and a driver that may be utilized to couple the elongate fixation member to the bone fragments from a lateral approach.

FIGS. 5B-5D illustrate a fourth step of some embodiments of the procedure, in which the first and second flexible tensioning elements 61, 62 may be pulled through the bone tunnels of the first bone fragment 1, the longitudinal passageway 104 of the elongate fixation member 150, and the second intramedullary canal 12 of the second bone fragment 2 via a retrieval wire (not shown) in FIGS. 5B-5D.

The elongate fixation member 150 may generally include a distal or first portion 101, a proximal or second portion 102, a central longitudinal axis 103, a longitudinal passageway 104, a first thread 151, a second thread 152, an intermediate portion 153, and a torque reception feature 154.

In some embodiments, the elongate fixation member 150 may comprise a compression screw design.

In some embodiments, the first thread 151 may comprise a first pitch, and the second thread 152 may comprise a second pitch that is different from the first pitch of the first thread 151. In these embodiments, the first and second bone fragments 1, 2 may be drawn toward each other in compression as the elongate fixation member 150 is inserted into the first and second intramedullary canals 11, 12, due to the differential thread pitches between the first and second threads 151, 152.

In some embodiments, the elongate fixation member 150 (and/or any other elongate fixation member described or contemplated herein) may comprise a resorbable material (such as PEEK, hydroxyapatite, etc.), and/or any other biocompatible material such as titanium, stainless steel, polymer, etc.

Figure 5E:
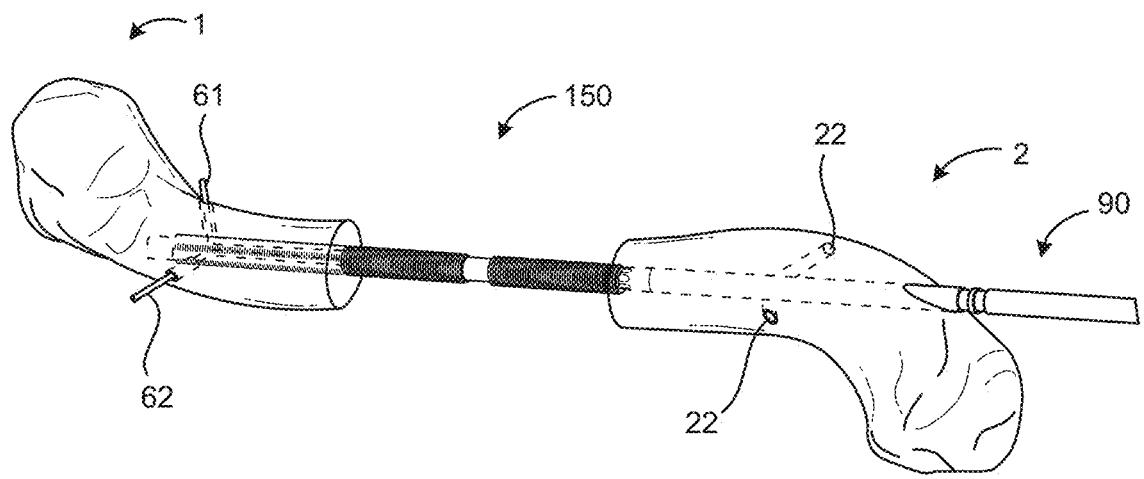
FIG. 5E illustrates a perspective side view of FIG. 5D with the driver coupled to the elongate fixation member.
Figure 5F:
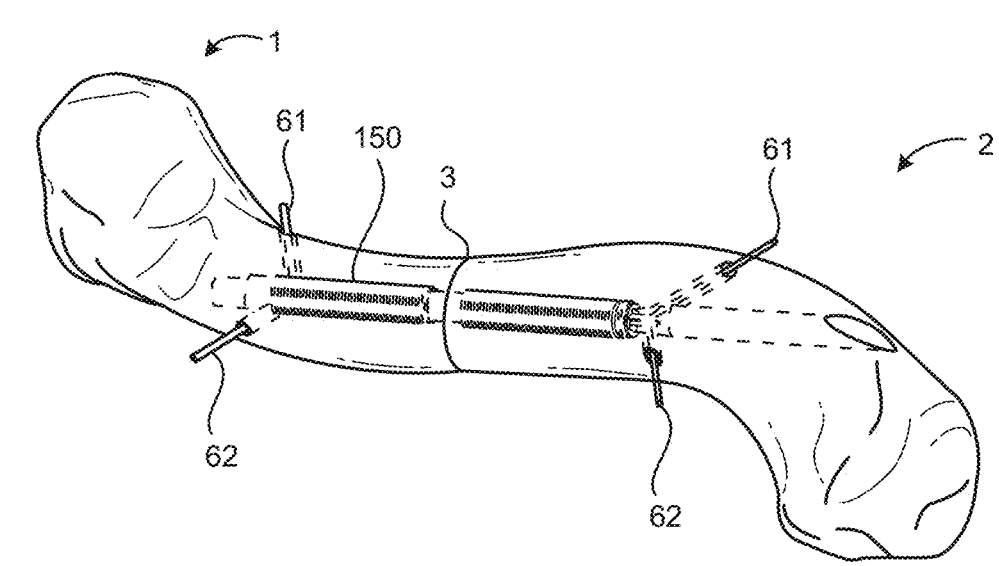
FIG. 5F illustrates a perspective side view of FIG. 5E with the elongate fixation member inserted within the intramedullary canals of the bone fragments and the flexible tensioning elements passing through the transverse bone tunnels.

FIGS. 5D-5F illustrate a fifth step of some embodiments of the procedure, in which the elongate fixation member 150 may be inserted into the first and second intramedullary canals 11, 12 of the first and second bone fragments 1, 2 from a lateral approach.

FIGS. 5D and 5E illustrate a driver 90 that may be utilized to couple the elongate fixation member 150 to the first and second bone fragments 1, 2. In some embodiments, the driver 90 may include a torque transmission feature 94 that may be configured to mate with a complementary shaped torque reception feature 154 formed within the longitudinal passageway 104 of the elongate fixation member 150 to drive the elongate fixation member 150 into the first and second intramedullary canals 11, 12 of the first and second bone fragments 1, 2. FIG. 5F shows the elongate fixation member 150 after it has been fully inserted into the first and second intramedullary canals 11, 12 and the bone fracture 3 has been reduced in compression by the compression screw design of the elongate fixation member 150.

FIG. 5F also illustrates a sixth step of some embodiments of the procedure, in which the first and second flexible tensioning elements 61, 62 may be pulled through the second transverse bone tunnels 22 of the second bone fragment 2 after the driver 90 is removed. This may be accomplished with one or more retrieval wires, as previously discussed.

Figure 5G:
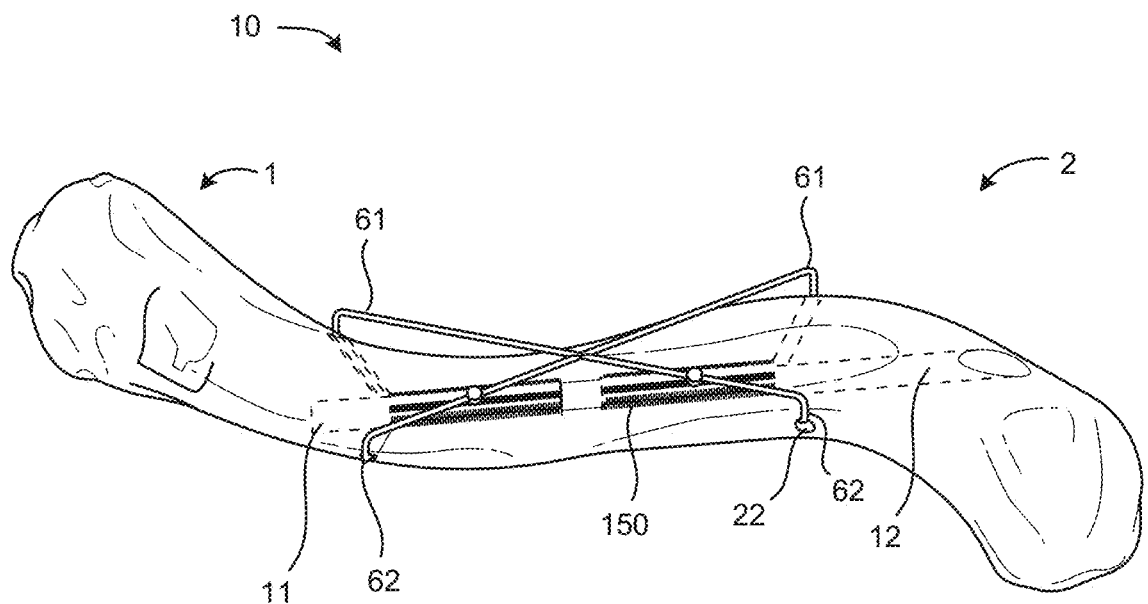
FIG. 5G illustrates a perspective side view of FIG. 5F with the flexible tensioning elements coupled to each other.
Figure 5H:
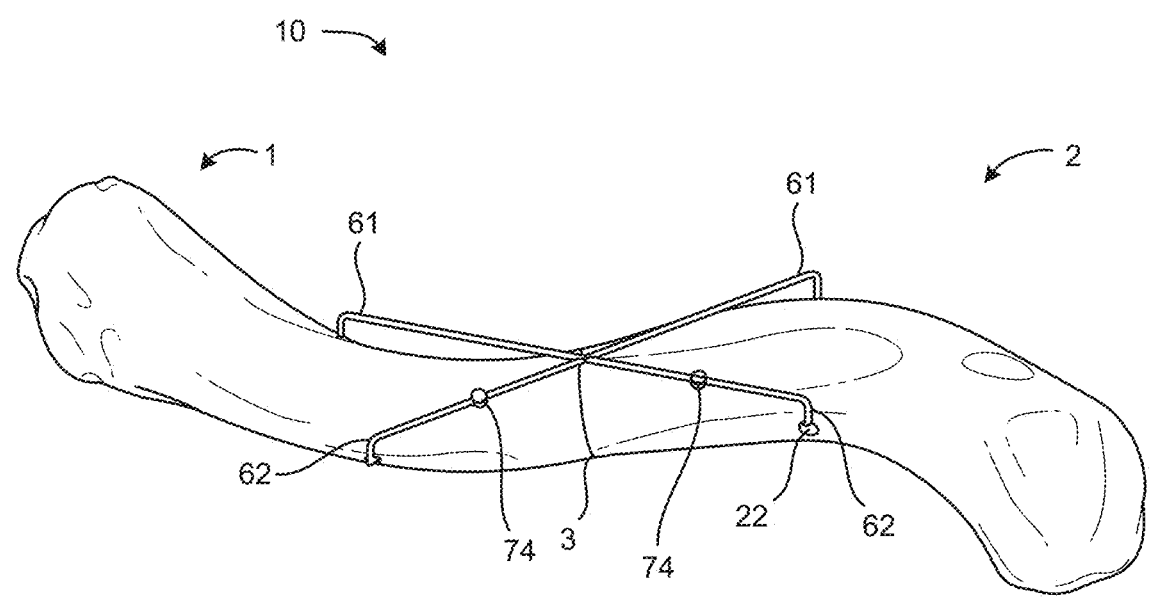
FIG. 5H illustrates another perspective side view of FIG. 5G.

FIGS. 5G and 5H illustrate a seventh step of some embodiments of the procedure, in which the first and second flexible tensioning elements 61, 62 may be coupled to each other and woven around the bone fracture 3 to further preload the bone fracture 3 in compression to resist tensile/distraction forces that may be imparted across the bone fracture 3, as previously described. Thus, combining the elongate fixation member 150 with the first and second flexible tensioning elements 61, 62 provides additional fixation, stabilization, and reduction of the bone fracture 3 over an elongate fixation member or flexible tensioning element alone.

In some embodiments, the first and second flexible tensioning elements 61, 62 may also be secured in place and/or tensioned via one or more fourth securing elements 74, which may include any of the securing element designs and/or tensioning element designs described or contemplated herein.

FIGS. 6A-6F illustrate example devices, instruments, and method steps for a bone fixation assembly and surgical procedure that may be performed from both a medial and lateral approach, according to another embodiment of the present disclosure.

In some embodiments, the first and second bone fragments 1, 2 may be prepared in a similar manner to the first bone fragment 1 shown in FIGS. 4A-4I in a first step and a second step. However, the first and second intramedullary canals 11, 12 of the first and second bone fragments 1, 2 may also be tapped with the tap tool 80 shown in FIG. 5A in a third step to form internal bone threads 81 within the first and second intramedullary canals 11, 12.

Figure 6A:
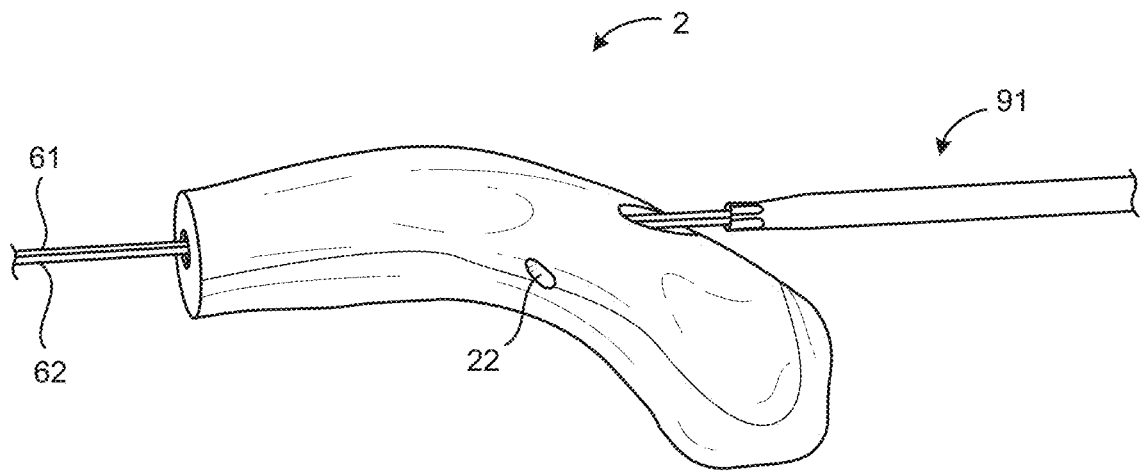
FIG. 6A illustrates a perspective side view of the prepared second bone fragment of FIG. 5D.
Figure 6B:
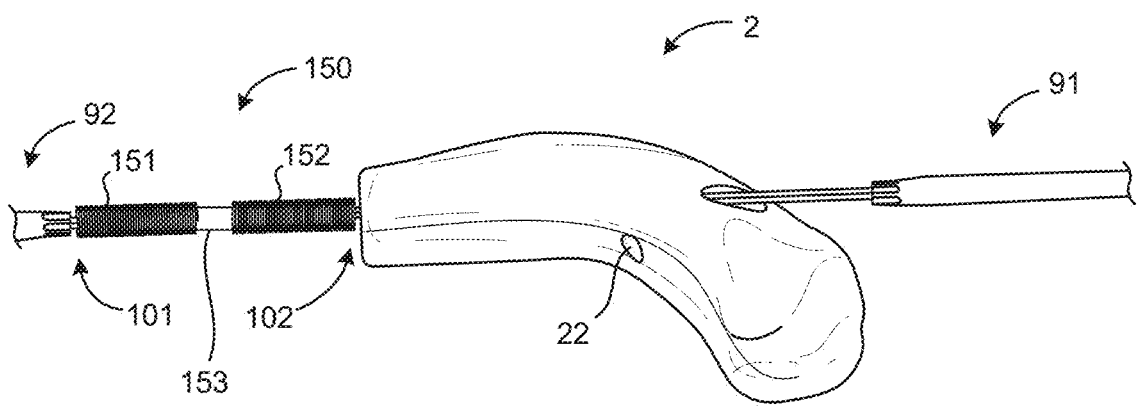
FIG. 6B illustrates a perspective side view of FIG. 6A with an elongate fixation member and first and second drivers that may be utilized to couple the elongate fixation member to the bone fragments from both a medial and a lateral direction, according to another embodiment of the present disclosure.

FIGS. 6A and 6B illustrate a fourth step of some embodiments of the procedure, in which the first and second flexible tensioning elements 61, 62 may be pulled through a first driver 91, the second intramedullary canal 12 of the second bone fragment 2, the elongate fixation member 150, and a second driver 92. This may be accomplished with one or more retrieval wires, as previously discussed.

Figure 6C:
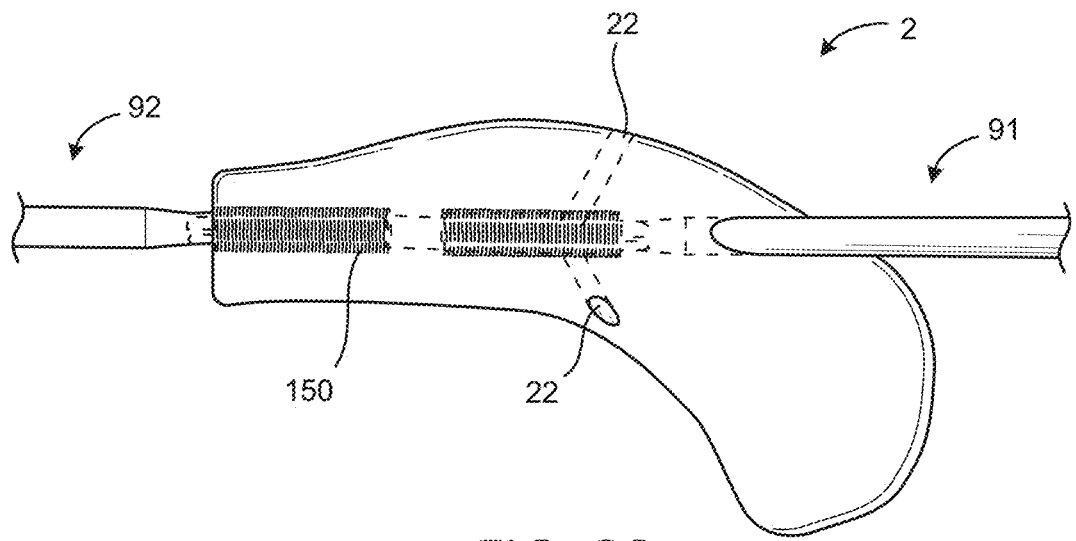
FIG. 6C illustrates a perspective side view of FIG. 6B with the second driver inserting the elongate fixation member into the intramedullary canal of the second bone fragment.

FIG. 6C illustrates a fifth step of some embodiments of the procedure, in which the second driver 92 may be utilized to drive the elongate fixation member 150 into the second intramedullary canal 12 of the second bone fragment 2 from a medial direction.

Figure 6D:
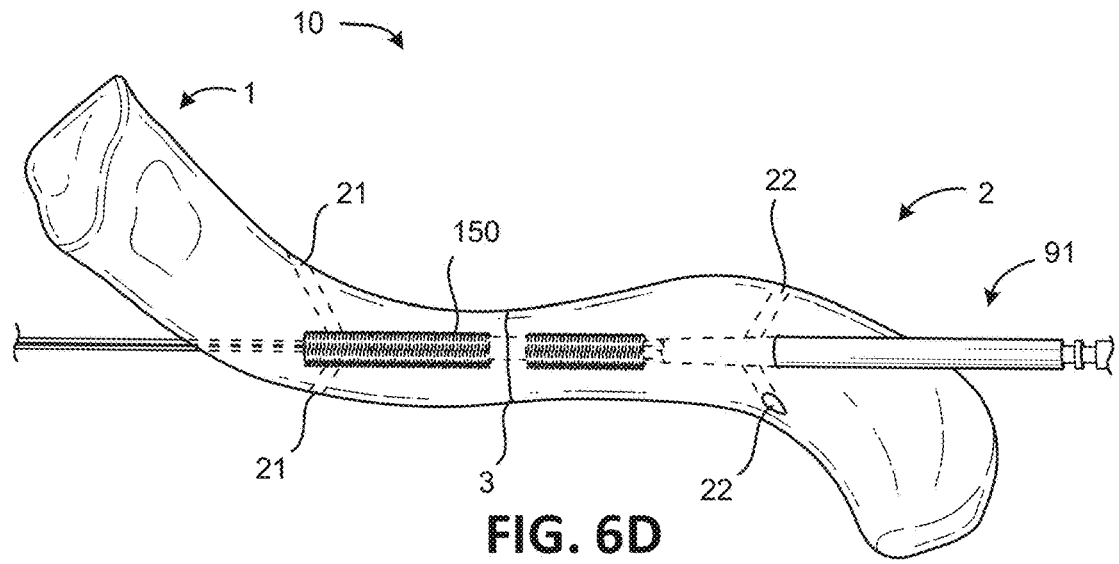
FIG. 6D illustrates a perspective side view of FIG. 6C with the first driver inserting the elongate fixation member into the intramedullary canal of the first bone fragment.

FIG. 6D illustrates a sixth step of some embodiments of the procedure, in which the first bone fragment 1 may be positioned adjacent the second bone fragment 2 and the first driver 91 may be utilized to drive the elongate fixation member 150 into the first intramedullary canal 11 of the first bone fragment 1 from a lateral direction in order to couple the elongate fixation member 150 to the first and second bone fragments 1, 2.

Figure 6E:
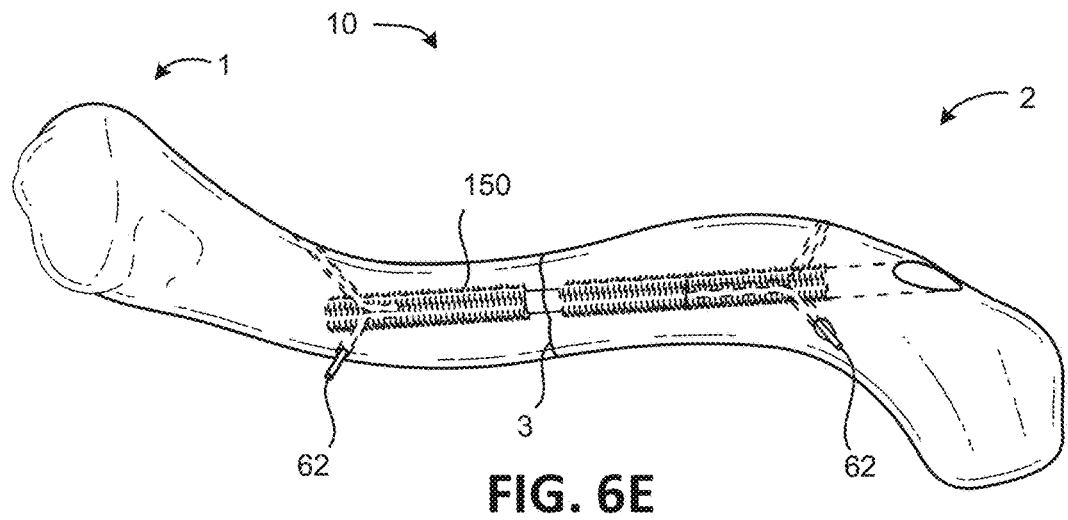
FIG. 6E illustrates a perspective side view of FIG. 6D with the elongate fixation member inserted into the intramedullary canals of the bone fragments and the flexible tensioning elements passing through the transverse bone tunnels.

FIG. 6E illustrates a seventh step of some embodiments of the procedure, in which the first and second flexible tensioning elements 61, 62 may be pulled through the first and second transverse bone tunnels 21, 22 of the bone fragments after the first and second drivers 91, 92 have been removed. This may be accomplished with one or more retrieval wires, as previously discussed.

Figure 6F:
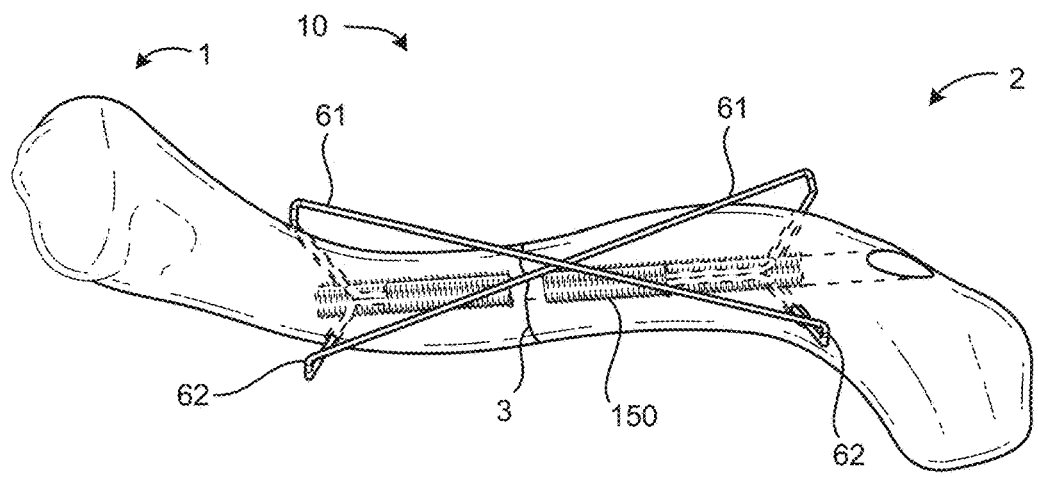
FIG. 6F illustrates a perspective side view of FIG. 6E with the flexible tensioning elements coupled to each other.

FIG. 6F illustrates an eighth step of some embodiments of the procedure, in which the first and second flexible tensioning elements 61, 62 may be coupled to each other and woven around the bone fracture 3 to preload the bone fracture 3 in compression to further resist tensile/distraction forces that may be imparted across the bone fracture 3, as previously described. Thus, combining the elongate fixation member 150 with the first and second flexible tensioning elements 61, 62 provides additional fixation, stabilization, and reduction of the bone fracture 3 over an elongate fixation member or flexible tensioning element alone.

In some embodiments, the first and second flexible tensioning elements 61, 62 may also be secured in place and/or tensioned via one or more securing elements (not shown), which may include any of the securing element designs and/or tensioning element designs described or contemplated herein.

FIGS. 7A-7D illustrate example devices, instruments, and method steps for a bone fixation assembly and surgical procedure, according to another embodiment of the present disclosure.

In some embodiments, the first and second bone fragments 1, 2 may be prepared in a similar manner to the first and second bone fragments 1, 2 shown in FIGS. 1B-1D in a first step and a second step.

Figure 7A:
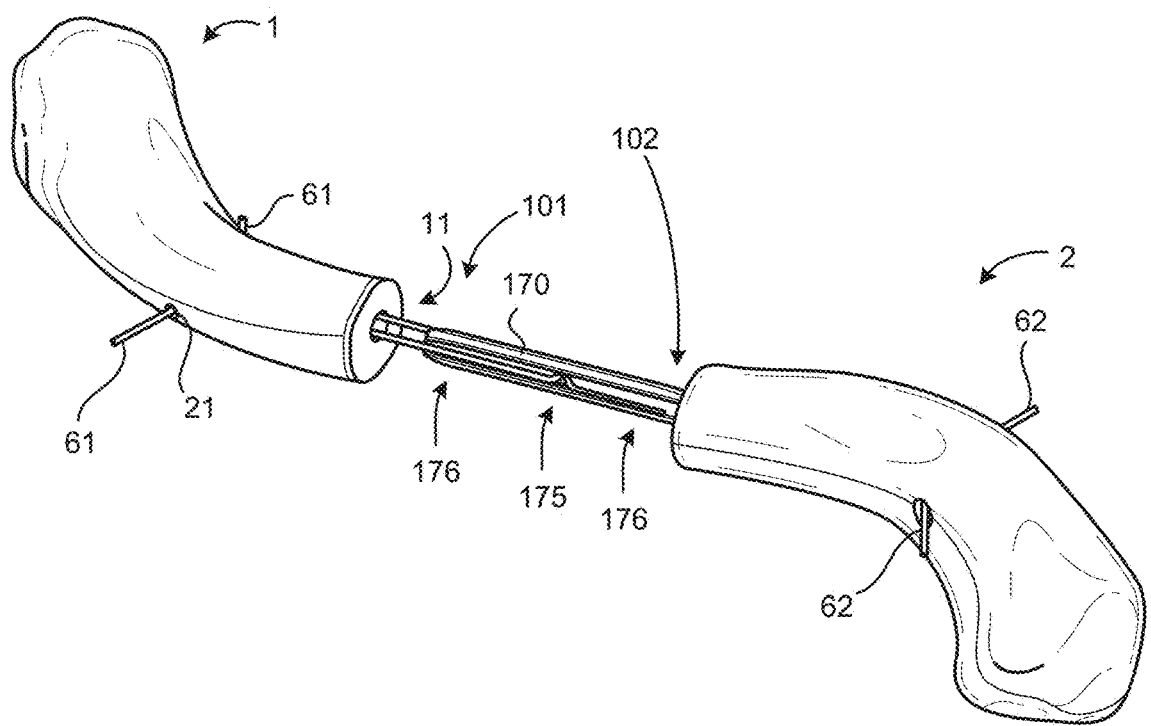
FIG. 7A illustrates a perspective side view of prepared bone fragments and an elongate fixation member, according to another embodiment of the present disclosure.

FIG. 7A illustrates a third step of some embodiments of the procedure, in which the first and second flexible tensioning elements 61, 62 may be passed through a centrally located transverse passageway 175 of an elongate fixation member 170, through the first and second intramedullary canals 11, 12, and out of the first and second transverse bone tunnels 21, 22. This may be accomplished with one or more retrieval wires, as previously discussed.

In some embodiments, the elongate fixation member 170 may include one or more grooves 176 formed in opposing sides of the elongate fixation member 170. The one or more grooves 176 may be configured to receive the first and second flexible tensioning elements 61, 62 therein to facilitate insertion of the elongate fixation member 170 into the first and second intramedullary canals 11, 12 by preventing frictional binding of the first and second flexible tensioning elements 61, 62 against the walls of the first and second intramedullary canals 11, 12.

Figure 7B:
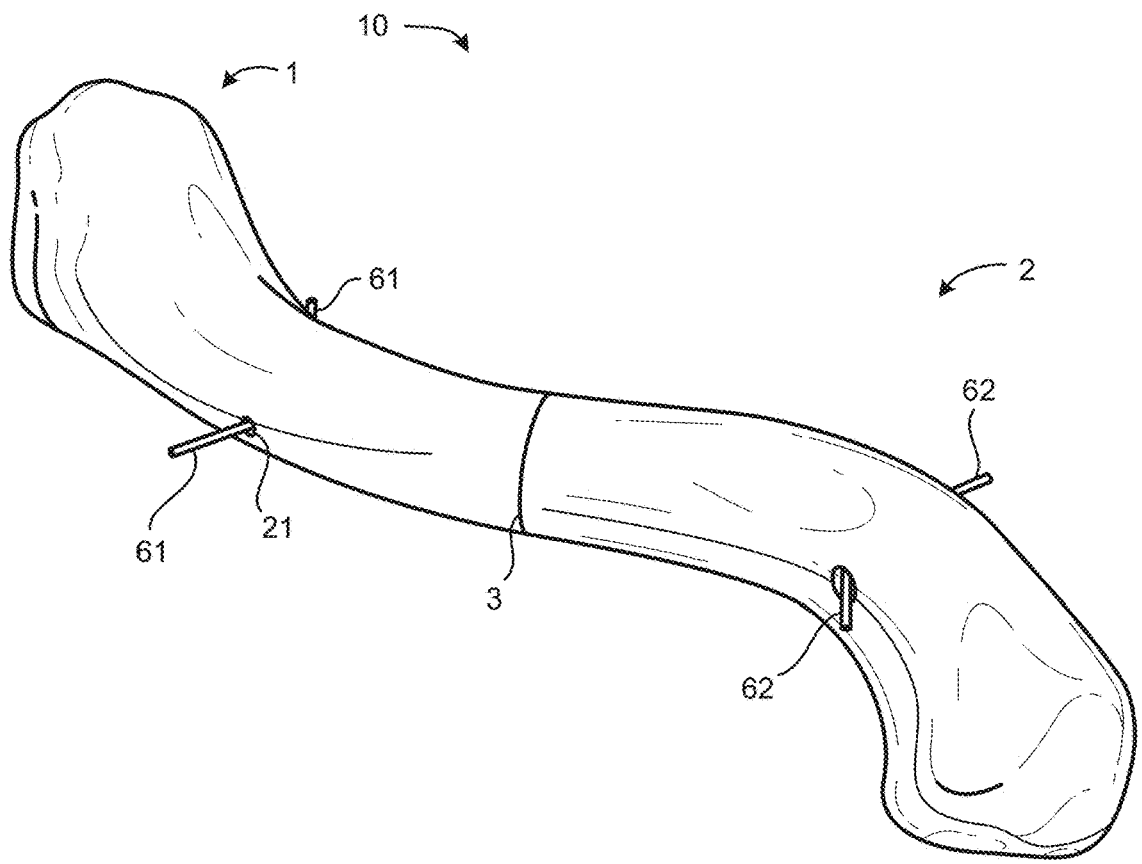
FIG. 7B illustrates a perspective side view of FIG. 7A with the elongate fixation member inserted into the bone fragments and flexible tensioning elements passing through transverse bone tunnels.
Figure 7C:
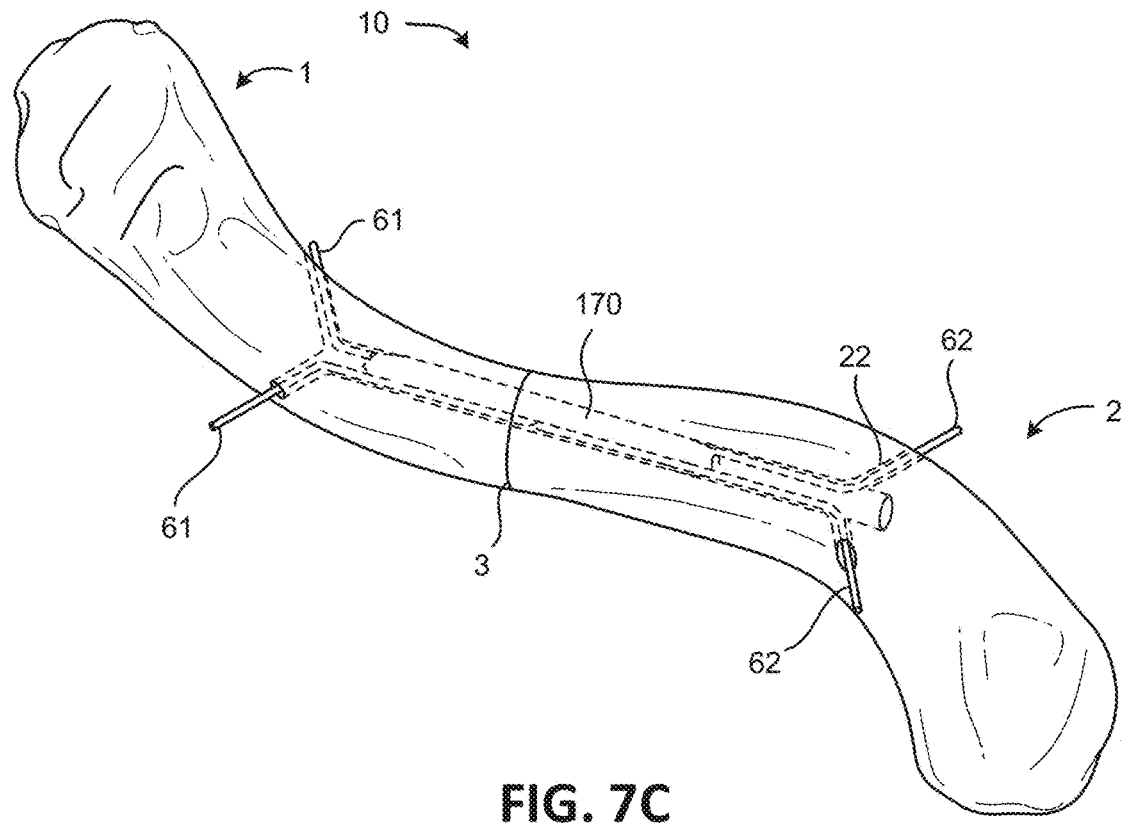
FIG. 7C illustrates another perspective side view of FIG. 7B.

FIGS. 7B and 7C illustrate a fourth step of some embodiments of the procedure, in which the elongate fixation member 170 may be inserted into the first and second intramedullary canals 11, 12 of the first and second bone fragments 1, 2 reducing the bone fracture 3.

Figure 7D:
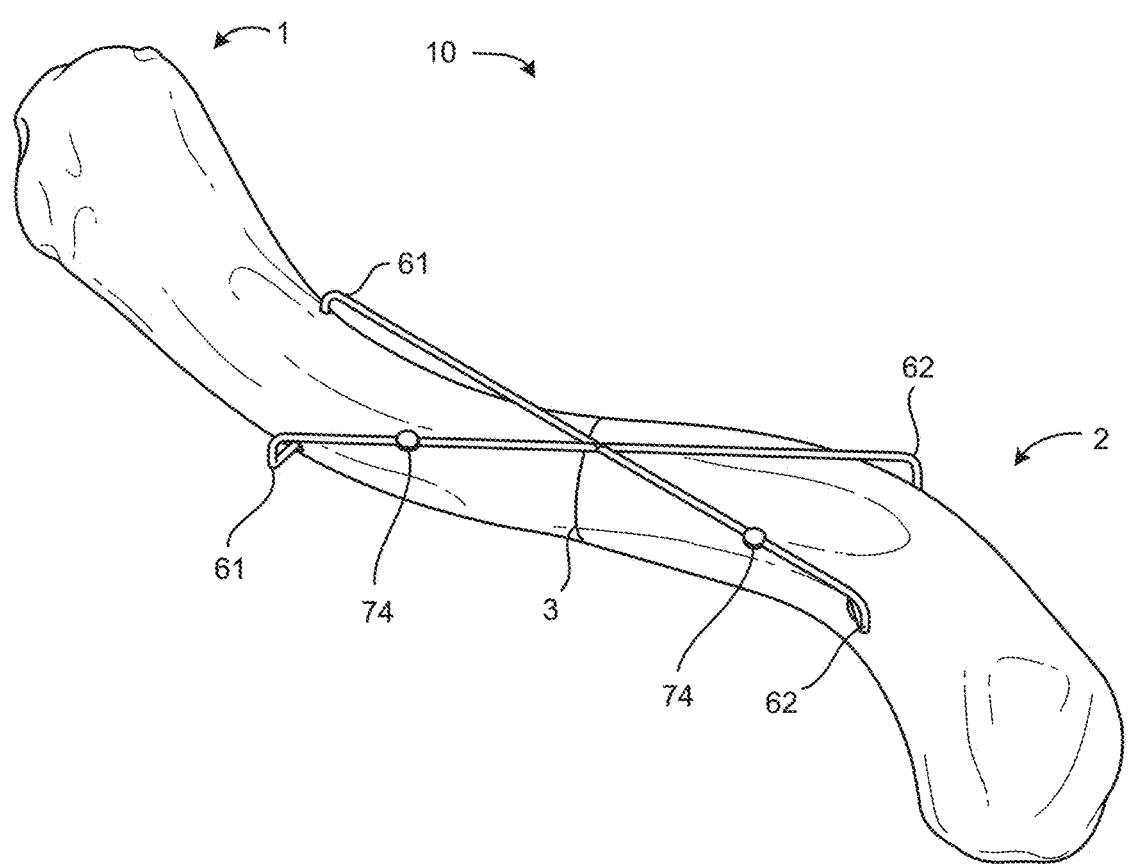
FIG. 7D illustrates a perspective side view of FIG. 7C with the flexible tensioning elements coupled to each other.

FIG. 7D illustrates a fifth step of some embodiments of the procedure, in which the first and second flexible tensioning elements 61, 62 may be coupled to each other and woven around the bone fracture 3 to preload the bone fracture 3 in compression to further resist tensile/distraction forces that may be imparted across the bone fracture 3, as previously described. Thus, combining the elongate fixation member 170 with the first and second flexible tensioning elements 61, 62 provides additional fixation, stabilization, and reduction of the bone fracture 3 over an elongate fixation member or flexible tensioning element alone.

In some embodiments, the first and second flexible tensioning elements 61, 62 may also be secured in place and/or tensioned via one or more fourth securing elements 74, which may include any of the securing element designs and/or tensioning element designs described or contemplated herein.

Figure 8A:
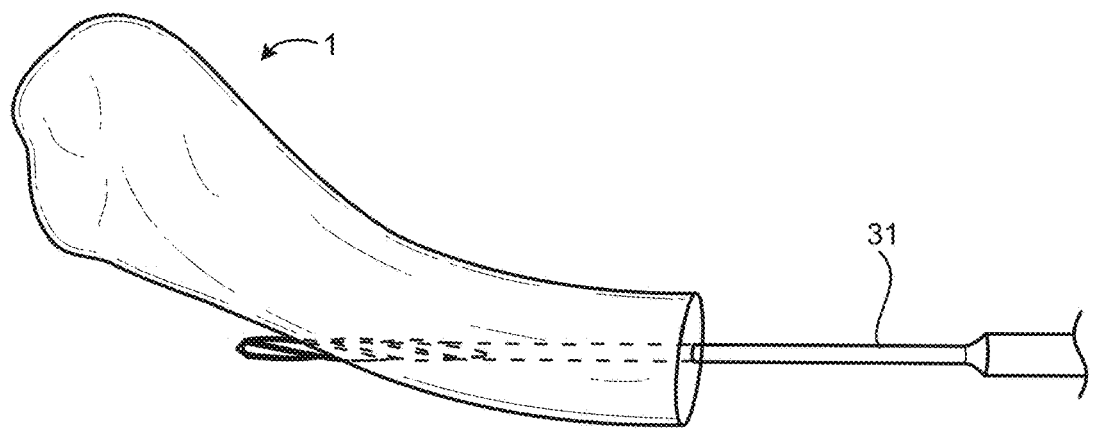
FIG. 8A illustrates a perspective side view of a drill bit preparing a pilot hole in a first bone fragment.
Figure 8B:
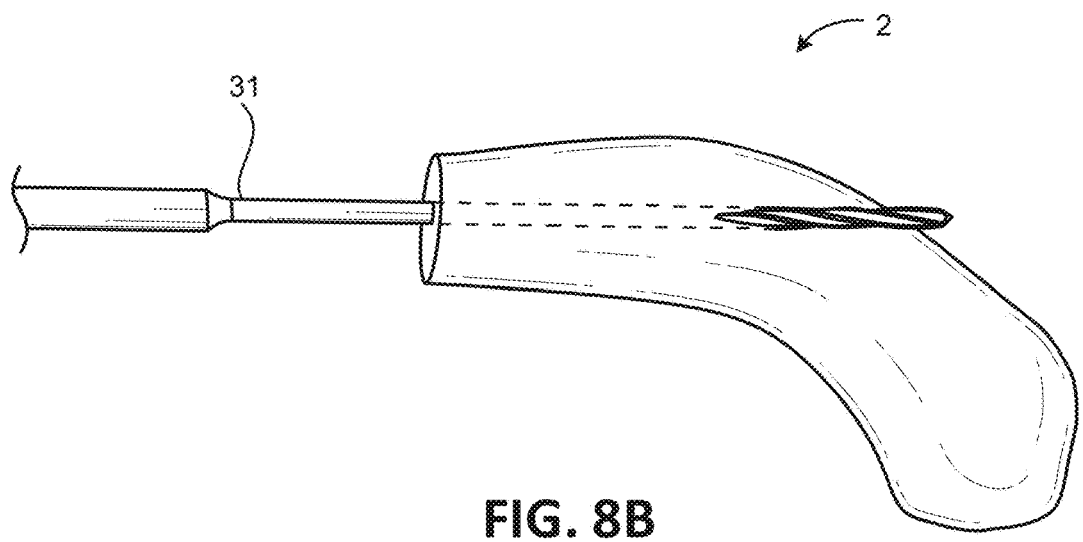
FIG. 8B illustrates a perspective side view of a drill bit preparing a pilot hole in a second bone fragment.
Figure 8C:
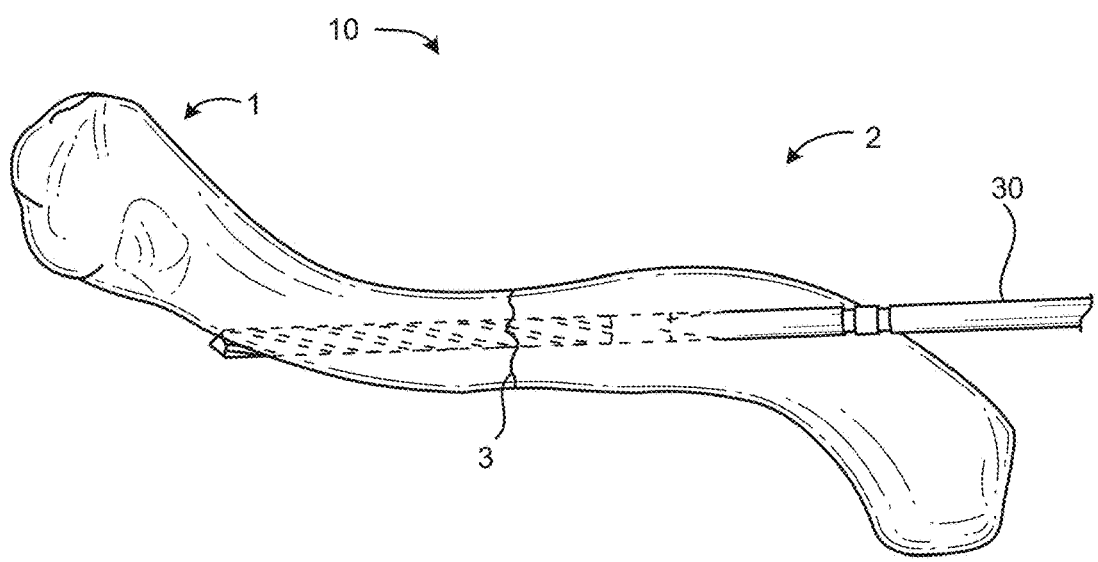
FIG. 8C illustrates a perspective side view of a reamer preparing the intramedullary canals of the bone fragments of FIGS. 8A and 8B from a lateral approach.
Figure 8D:
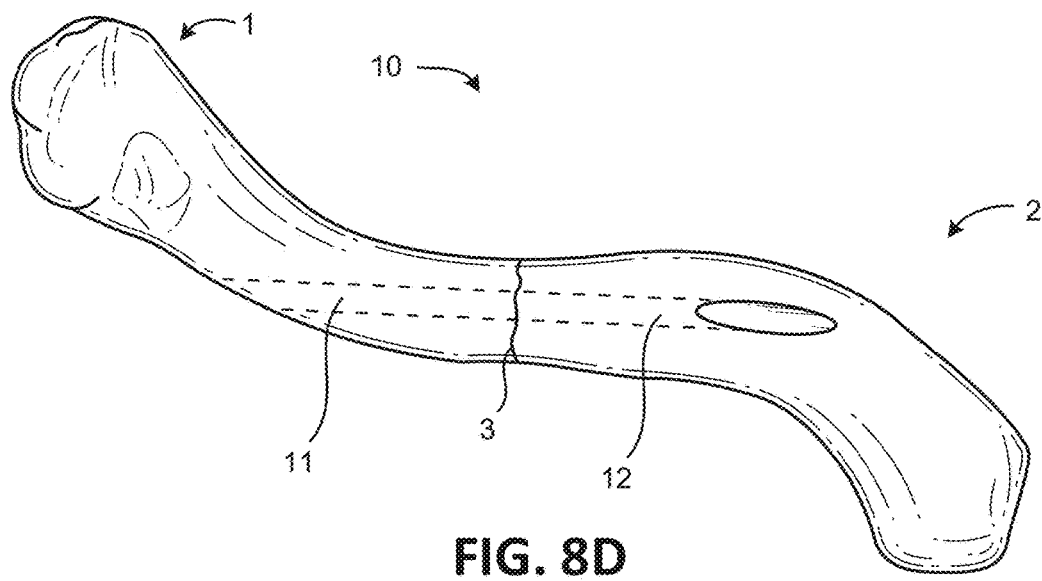
FIG. 8D illustrates a perspective side view of FIG. 8C showing the prepared intramedullary canals.
Figure 8E:
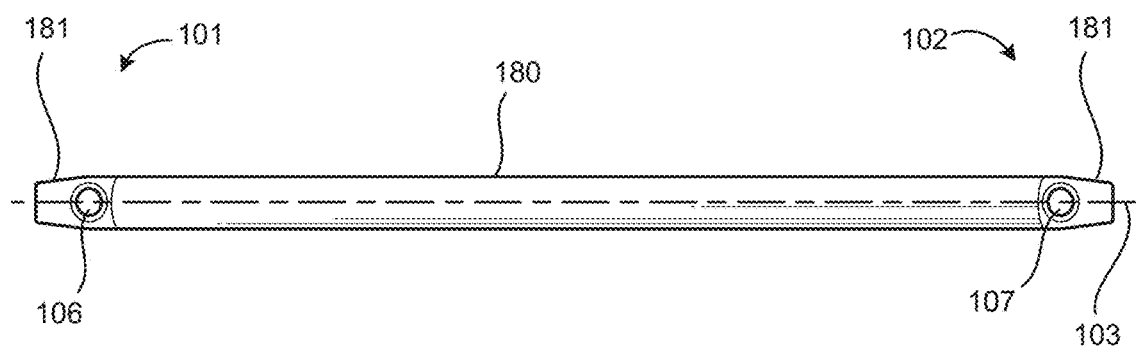
FIG. 8E illustrates a side view of an elongate fixation member, according to another embodiment of the present disclosure.
Figure 8F:
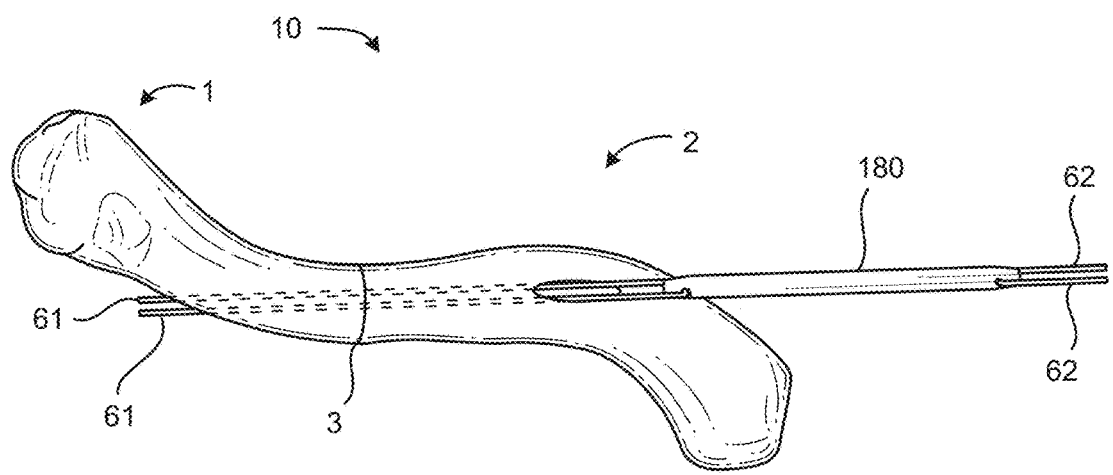
FIG. 8F illustrates a perspective side view of FIG. 8D with the elongate fixation member of FIG. 8E being inserted into the bone fragments from a lateral approach.
Figure 8G:
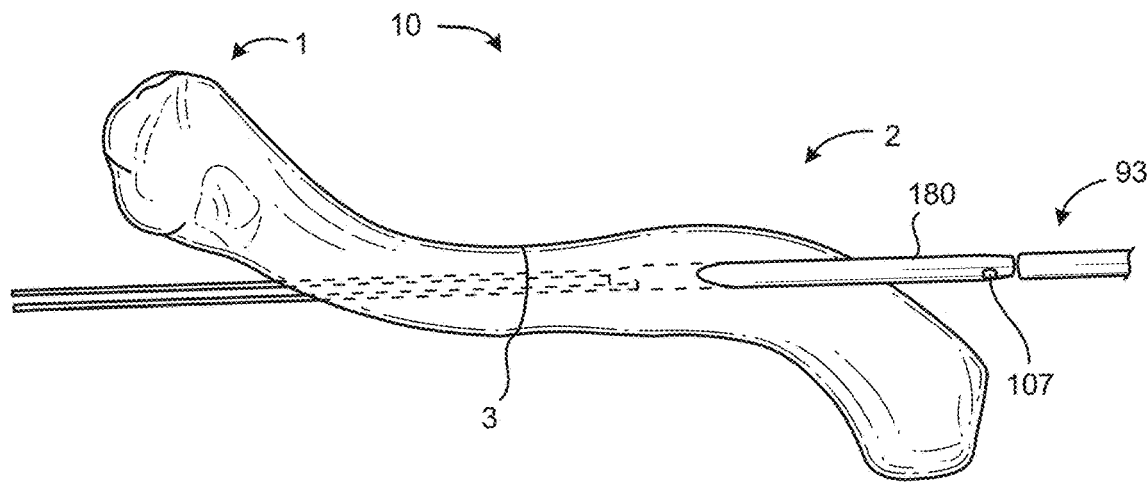
FIG. 8G illustrates a perspective side view of FIG. 8F with an impact tool driving the elongate fixation member into the bone fragments.
Figure 8H:
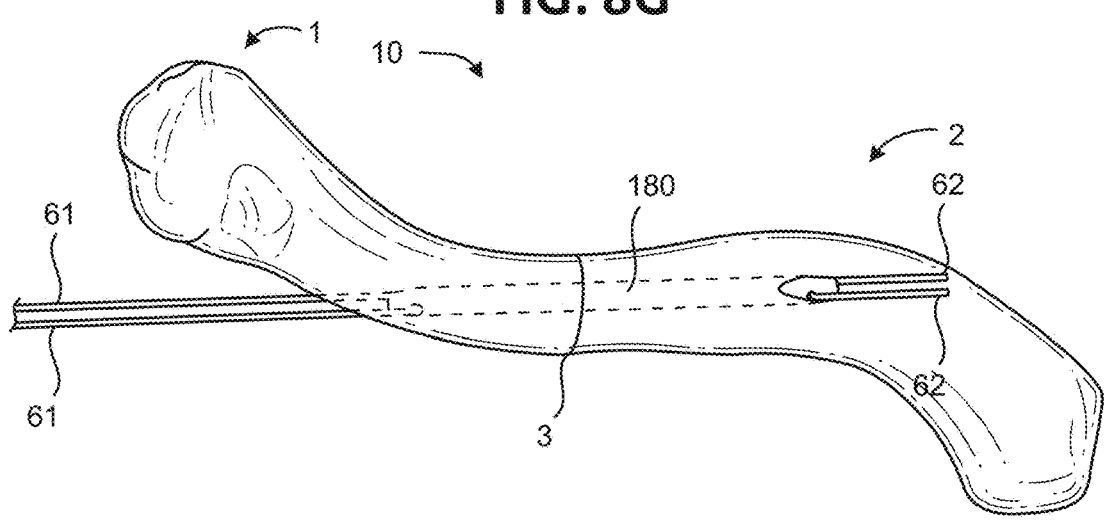
FIG. 8H illustrates a perspective side view of FIG. 8G with the elongate fixation member inserted into the bone fragments and flexible tensioning elements coupled to the elongate fixation member.
Figure 8I:
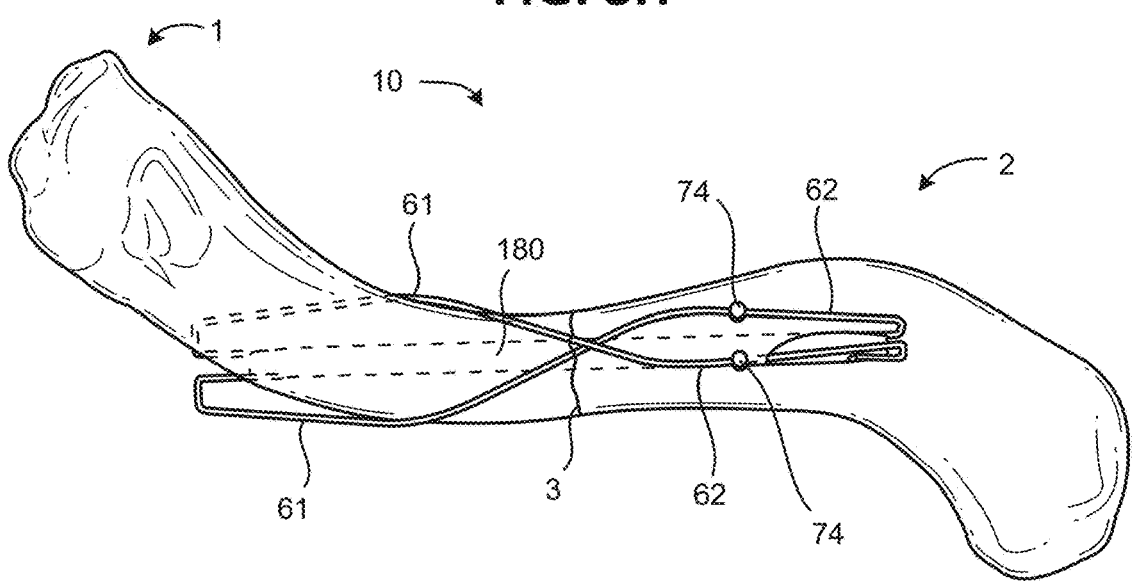
FIG. 8I illustrates a perspective side view of FIG. 8H with the flexible tensioning elements coupled to each other.
Figure 8J:
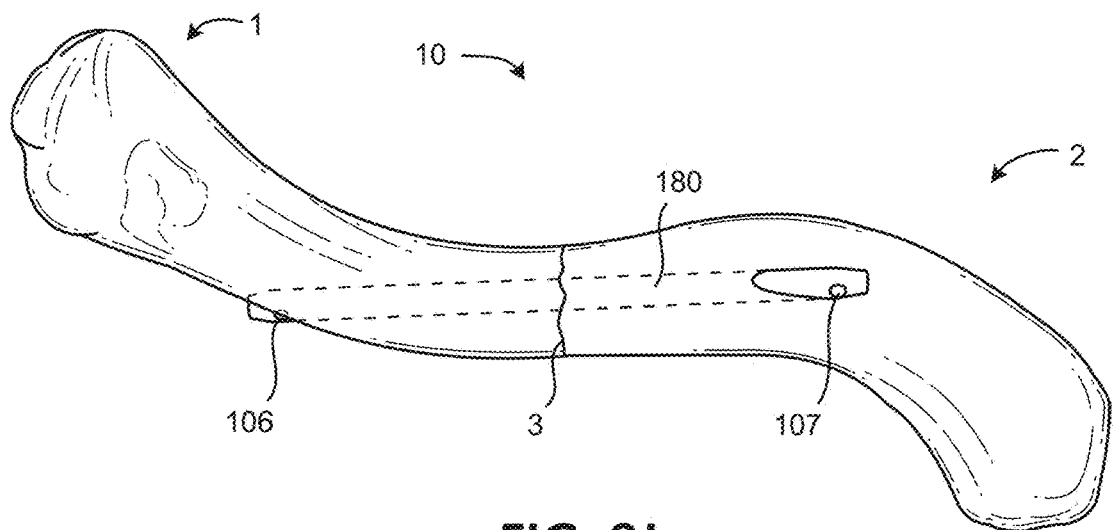
FIG. 8J illustrates a perspective side view of FIG. 8J without flexible tensioning elements.
Figure 8K:
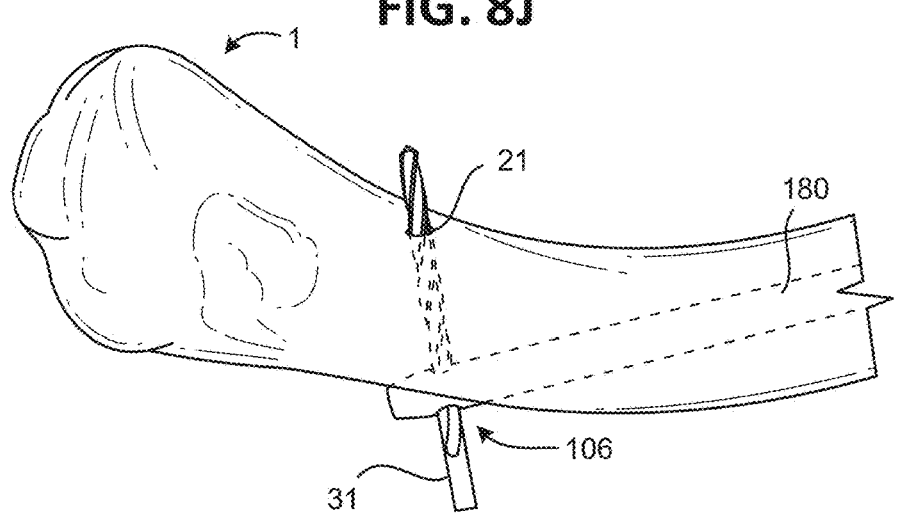
FIG. 8K illustrates a perspective side view of FIG. 8J with a drill bit forming a transverse bone tunnel through the first bone fragment.
Figure 8L:
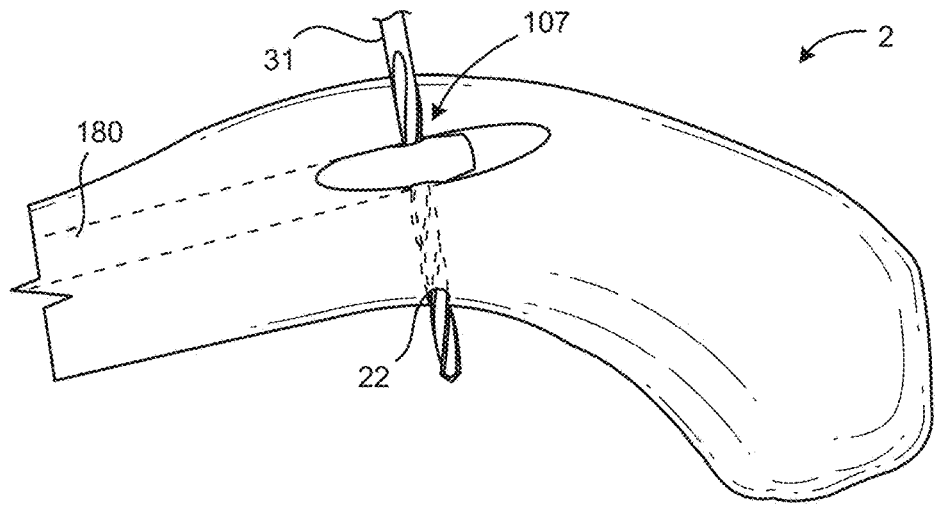
FIG. 8L illustrates a perspective side view of FIG. 8J with a drill bit forming a transverse bone tunnel through the second bone fragment.
Figure 8M:
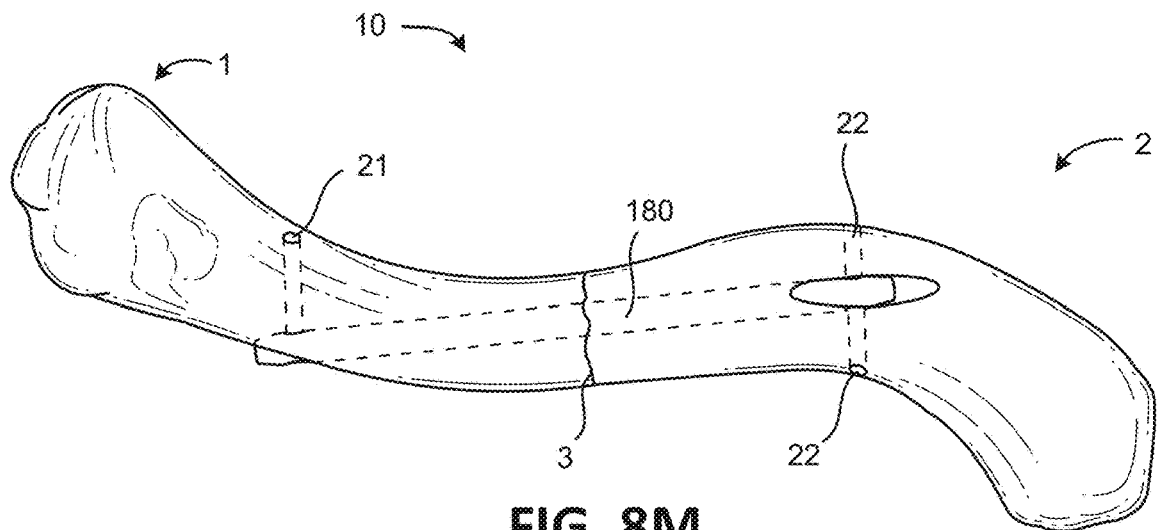
FIG. 8M illustrates another perspective side view of the first and second bone fragments of FIGS. 8K and 8L.
Figure 8N:
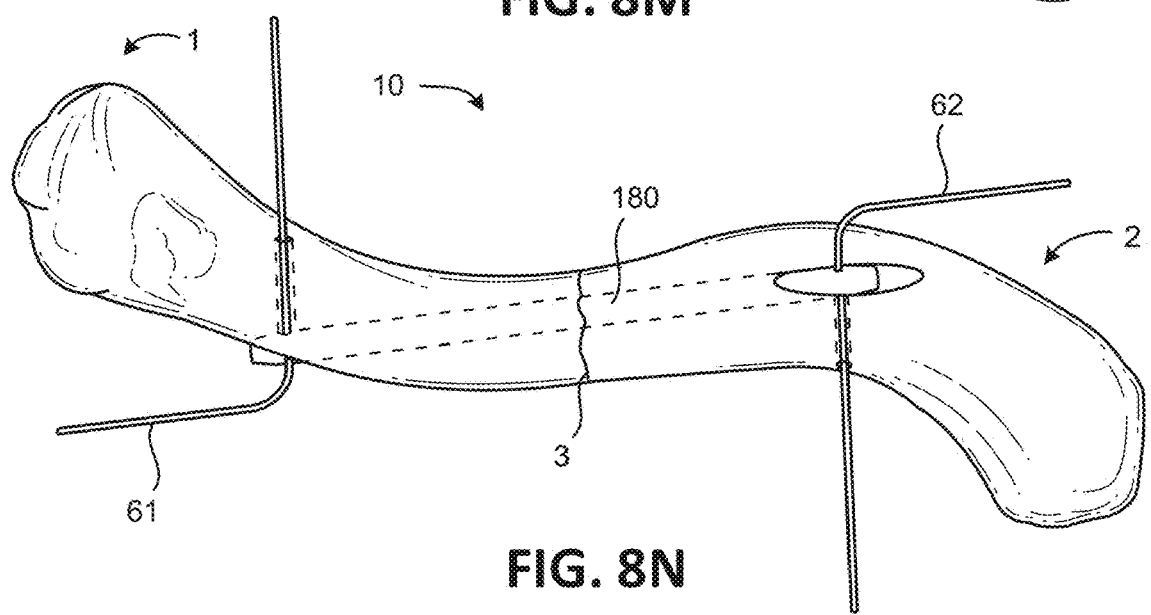
FIG. 8N illustrates a perspective side view of FIG. 8M with flexible tensioning elements passing through the transverse bone tunnels.
Figure 8O:
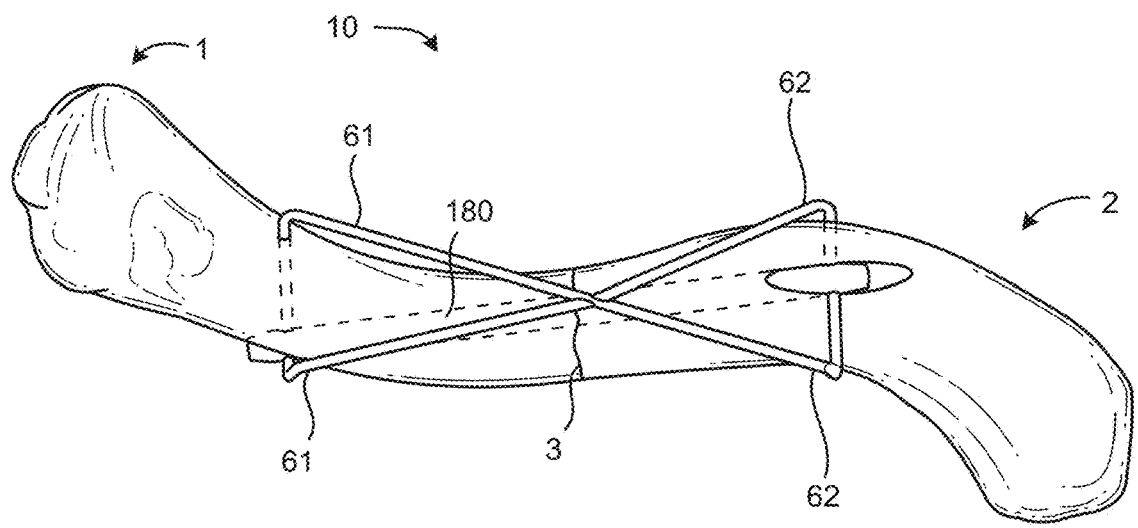
FIG. 8O illustrates a perspective side view of FIG. 8N with the flexible tensioning elements coupled to each other.

FIGS. 8A-8O illustrate example devices, instruments, and method steps for a bone fixation assembly and one or more simplified surgical procedures, according to embodiments of the present disclosure.

FIGS. 8A and 8B illustrate a first step of some embodiments of a simplified procedure, in which a drill bit 31 may be utilized to create pilot holes through the first and second intramedullary canals 11, 12 of the first and second bone fragments 1, 2.

FIGS. 8C and 8D illustrate a second step of some embodiments of the simplified procedure, in which the first and second bone fragments 1, 2 may be aligned with each other to reduce the bone fracture 3 and a reamer 30 may then be utilized to enlarge or ream out the pilot holes of FIGS. 8A and 8B in order to create prepared first and second intramedullary canals 11, 12 that are aligned with each other. In some embodiments, the reamer 30 may be utilized from a lateral direction. However, it will be understood that in other embodiments the reamer 30 may be utilized from a medial direction.

FIG. 8E illustrates an elongate fixation member 180, according to another embodiment of the present disclosure. The elongate fixation member 180 may generally include a distal portion or first portion 101, a proximal portion or second portion 102, and a central longitudinal axis 103.

In some embodiments, the proximal and/or distal portions 101, 102 may comprise tapered ends 181 to facilitate insertion of the elongate fixation member 180 into bone.

In some embodiments, the elongate fixation member 180 may include a first transverse passageway 106 configured to receive a first flexible tensioning element 61 therethrough from a first direction that may be transverse to the central longitudinal axis 103 of the elongate fixation member 180. The elongate fixation member 180 may also include a second transverse passageway 107 configured to receive a second flexible tensioning element 62 therethrough from a second direction that may be transverse to the central longitudinal axis 103 of the elongate fixation member 180.

In some embodiments, the first direction and the second direction may be the same, or similar to each other.

In some embodiments, the first direction and the second direction may be opposite from each other.

In some embodiments, the elongate fixation member 180 may comprise an intramedullary rod.

In some embodiments, the elongate fixation member 180 may include a generally cylindrical shape.

In some embodiments, the elongate fixation member 180 may be solid or substantially solid. However, it will also be understood that in some embodiments the elongate fixation member 180 may comprise an at least partially hollow interior.

In some embodiments, the elongate fixation member 180 may comprise a rigid material to provide rigid fixation of the first and second bone fragments 1, 2 relative to each other.

FIGS. 8F-8H illustrate a third step of some embodiments of the simplified procedure, in which the elongate fixation member 180 may be inserted into the first and second intramedullary canals 11, 12 of the first and second bone fragments 1, 2. FIG. 8F shows the first flexible tensioning element 61 passing through the first and second intramedullary canals 11, 12. This may be accomplished with one or more retrieval wires, as previously discussed. FIG. 8G shows the elongate fixation member 180 being forced into the first and second intramedullary canals 11, 12 with an impact driver tool 93, and FIG. 8H shows the elongate fixation member 180 placed within the first and second intramedullary canals 11, 12.

FIG. 8I illustrates a fourth step of some embodiments of the simplified procedure, in which the first and second flexible tensioning elements 61, 62 may be woven around the bone fracture 3 and secured together. The first and second flexible tensioning elements 61, 62 may be configured to span the bone fracture 3 and preload the bone fracture 3 in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 180 with the first and second flexible tensioning elements 61, 62.

In some embodiments, the first and second flexible tensioning elements 61, 62 may also be secured in place and/or tensioned via one or more fourth securing elements 74, which may include any of the securing element designs and/or tensioning element designs described or contemplated herein.

FIGS. 8J-8O illustrate example devices, instruments, and method steps for a bone fixation assembly and an alternative simplified surgical procedure, according to another embodiment of the present disclosure.

In some embodiments, the first and second bone fragments 1, 2 may be prepared in a similar manner to the first and second bone fragments 1, 2 shown in FIGS. 8A-8D in a first step and a second step.

FIG. 8J illustrates a third step of some embodiments of the alternative simplified procedure, in which the elongate fixation member 180 may be inserted into the first and second intramedullary canals 11, 12 of the first and second bone fragments 1, 2 without the first and second flexible tensioning elements 61, 62 being coupled to the elongate fixation member 180.

FIGS. 8K-8M illustrate a fourth step of some embodiments of the alternative simplified procedure, in which the first and second transverse bone tunnels 21, 22 may be formed through the first and second bone fragments 1, 2 with a drill bit 31.

In some embodiments, the first and second transverse passageways 106, 107 of the elongate fixation member 180 may be utilized to guide the drill bit 31 through the first and second bone fragments 1, 2 to quickly form the first and second transverse bone tunnels 21, 22 therethrough.

FIG. 8N illustrates a fifth step of some embodiments of the alternative simplified procedure, in which the first and second flexible tensioning elements 61, 62 may be inserted through the first and second transverse bone tunnels 21, 22 and through the first and second transverse passageways 106, 107 of the elongate fixation member 180.

FIG. 8O illustrates a sixth step of some embodiments of the alternative simplified procedure, in which the first and second flexible tensioning elements 61, 62 may be woven around the bone fracture 3 and secured together. The first and second flexible tensioning elements 61, 62 may be configured to span the bone fracture 3 and preload the bone fracture 3 in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 180 with the first and second flexible tensioning elements 61, 62.

In some embodiments, the first and second flexible tensioning elements 61, 62 may also be secured in place and/or tensioned via one or more securing elements (not shown), which may include any of the securing element designs and/or tensioning element designs described or contemplated herein.

FIGS. 9A-9E illustrate example devices, instruments, and method steps for a bone fixation assembly and procedure, according to another embodiment of the present disclosure.

Figure 9A:
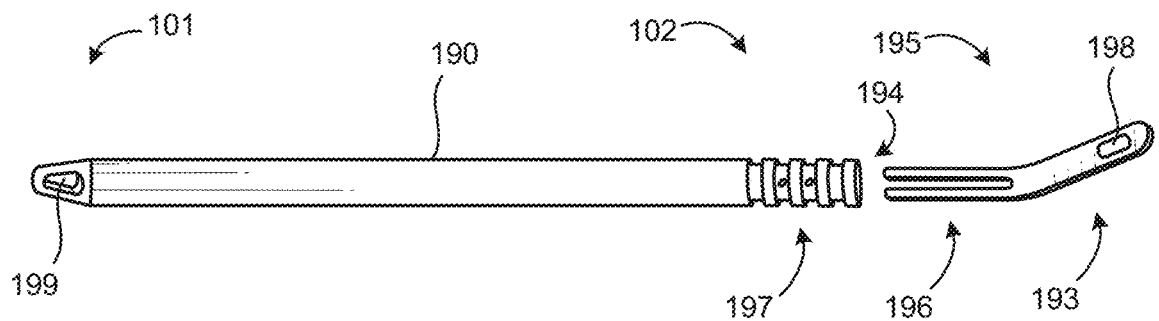
FIG. 9A illustrates a perspective side view of an elongate fixation member including a tensioner element, according to another embodiment of the present disclosure.

FIG. 9A illustrates an elongate fixation member 190 couplable with a tensioner element 195, according to an embodiment of the present disclosure.

The elongate fixation member 190 may include a distal or first portion 101, a proximal or second portion 102, an eyelet 199 at the distal portion, one or more attachment features 197, and a recess 194 formed in the proximal portion of the elongate fixation member 190.

The tensioner element 195 may include an attachment member 196, a resilient member 193, and an opening 198 formed in the resilient member 193.

In some embodiments, the resilient member 193 may be slightly angled with respect to the attachment member 196 in a free state.

Figure 9B:
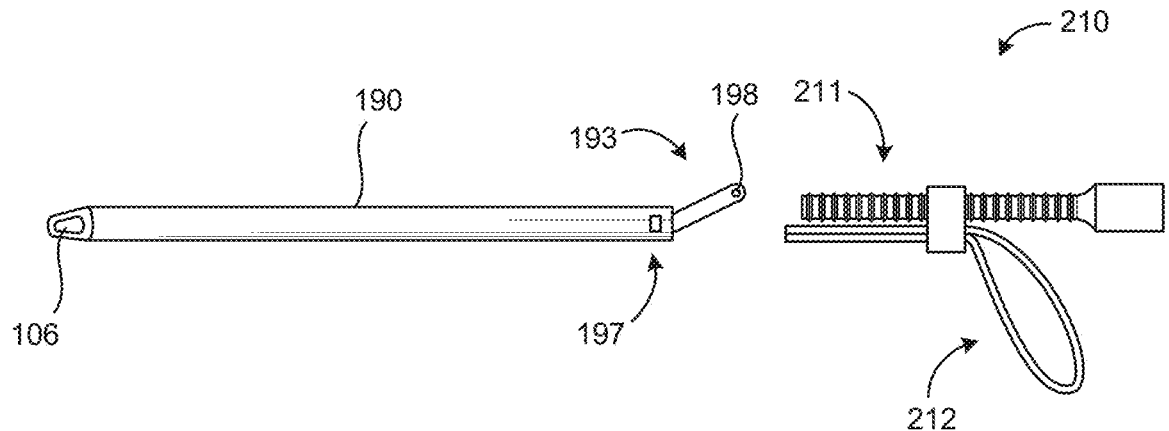
FIG. 9B illustrates a side view of the elongate fixation member of FIG. 9A and a bending tool, according to an embodiment of the present disclosure.
Figure 9C:
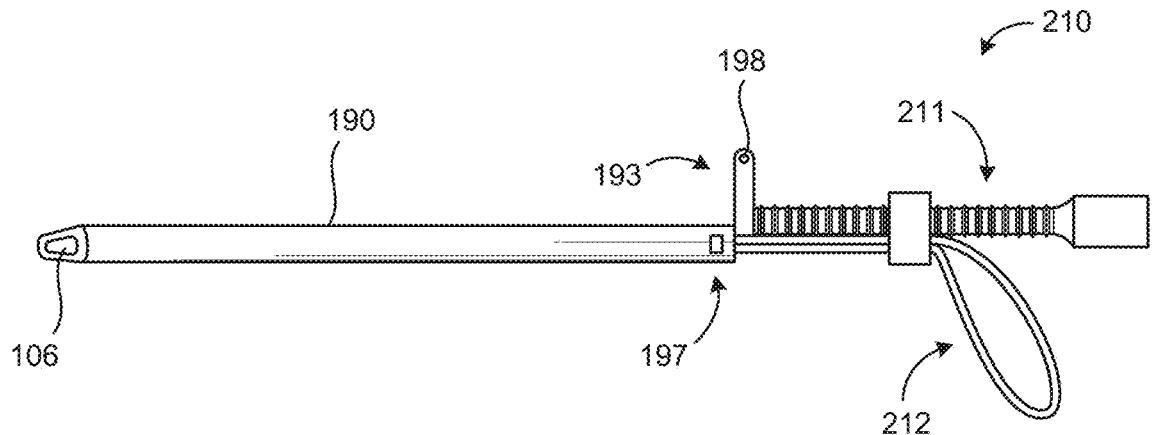
FIG. 9C illustrates a side view of FIG. 9B with the bending tool coupled to the elongate fixation member and engaging the tensioner element.
Figure 9D:
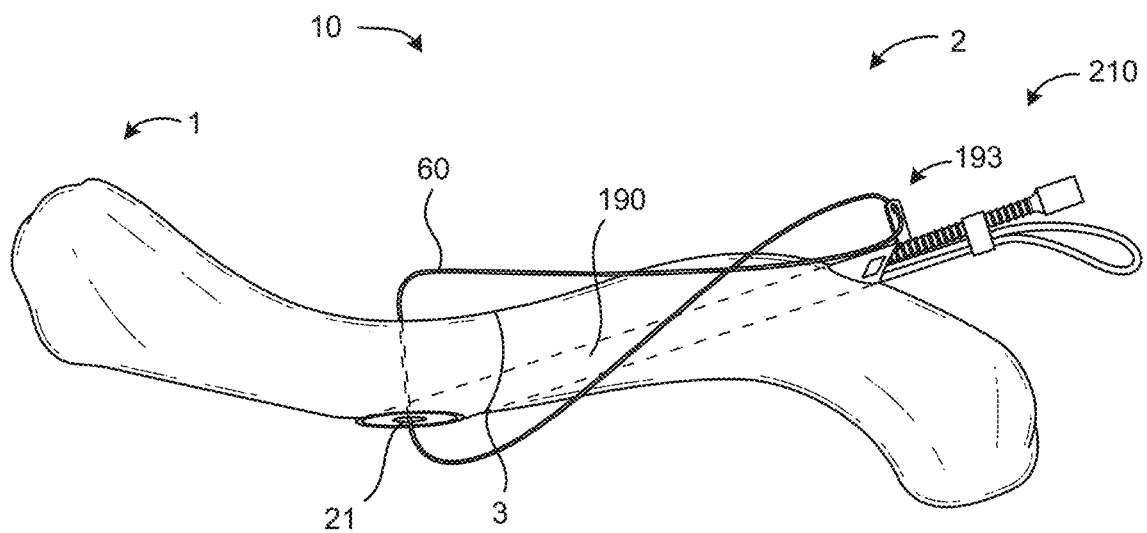
FIG. 9D illustrates a perspective side view FIG. 9C with the elongate fixation member inserted into a fractured bone and a flexible tensioning element passing through the tensioner element.
Figure 9E:
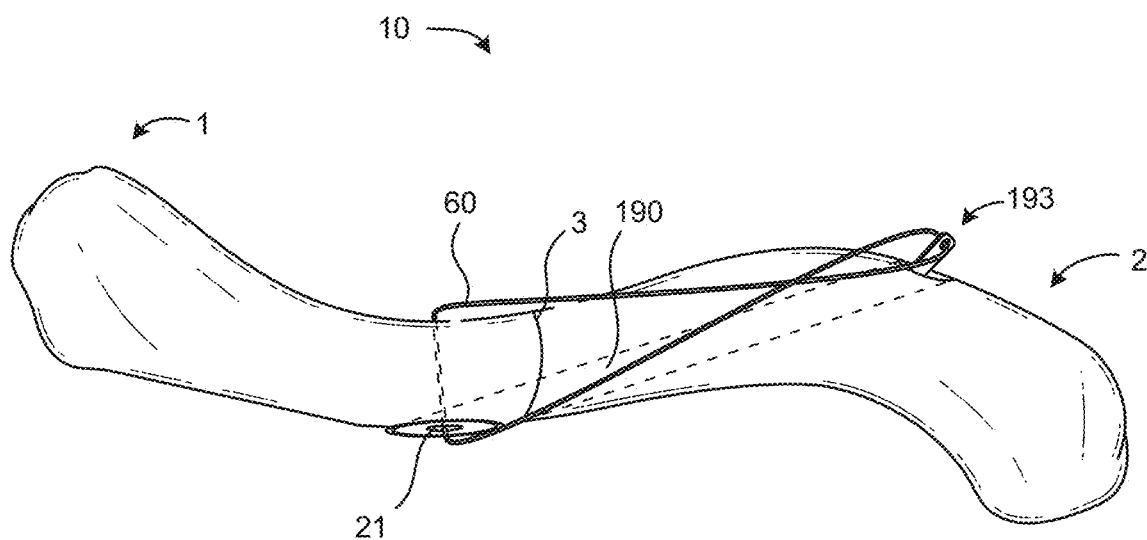
FIG. 9E illustrates a perspective side view of FIG. 9D with the bending tool removed from the elongate fixation member.

In some embodiments, the tensioner element 195 may comprise a super elastic material (e.g., such as nitinol, etc.)

that may be configured to provide a tensioning force to the flexible tensioning element 60, as shown in FIGS. 9D and 9E.

In some embodiments, the attachment member 196 may be received within the recess 194 formed in the proximal portion of the elongate fixation member 190 to removably couple the tensioner element 195 with the elongate fixation member 190.

In some embodiments, the tensioner element 195 may be integrally formed with, or otherwise permanently attached to, the elongate fixation member 190.

In some embodiments, the elongate fixation member 190 may comprise a resorbable material (such as PEEK, hydroxyapatite, etc.) and/or any other biocompatible material such as titanium, stainless steel, polymer, etc.

FIGS. 9B and 9C illustrate the elongate fixation member 190 of FIG. 9A in conjunction with an actuation tool 210, according to an embodiment of the present disclosure.

In some embodiments, the actuation tool 210 may include an actuator 211 coupled with a handle 212.

In some embodiments, the actuation tool 210 may also include one or more attachment features (not shown) which may be configured to engage with the one or more attachment features 197 of the elongate fixation member 190 to removably couple the actuation tool 210 with the elongate fixation member 190, as shown in FIGS. 9C and 9D.

In some embodiments, the actuator 211 may comprise a threaded thumb screw which may be advanced toward the resilient member 193 via rotation in a first direction to bend the resilient member 193 forward, as shown in FIGS. 9C and 9D.

In some embodiments, the resilient member 193 of the tensioner element 195 may be bent to about 90 degrees when fully loaded by the actuator 211.

In some embodiments, the actuator 211 may be retracted from the resilient member 193 via rotation in a second direction to release the resilient member 193 and/or remove the actuation tool 210 from the elongate fixation member 190, as shown in FIGS. 9B and 9E.

FIG. 9D illustrates the elongate fixation member 190 inserted into a bone 10 and a flexible tensioning element 60 passing through the opening 198 in the resilient member 193 with the actuation tool 210 attached to the elongate fixation member 190 and applying a bending force to the resilient member 193. In this manner, the surgeon can couple the flexible tensioning element 60 to the resilient member 193 as tight as possible while the resilient member 193 is bent forward by the actuator 211.

FIG. 9E illustrates the bone fixation assembly of FIG. 9D with the actuation tool 210 removed from the elongate fixation member 190, thus allowing the resilient member 193 to pull the flexible tensioning element 60 even tighter and further preload the bone fracture 3 in compression to resist tensile/distraction forces that may be imparted across the bone fracture 3, as previously described.

FIGS. 10A-11B illustrate various alternative devices and methods for tensioning a flexible tensioning element, according to embodiments of the present disclosure.

Figure 10A:
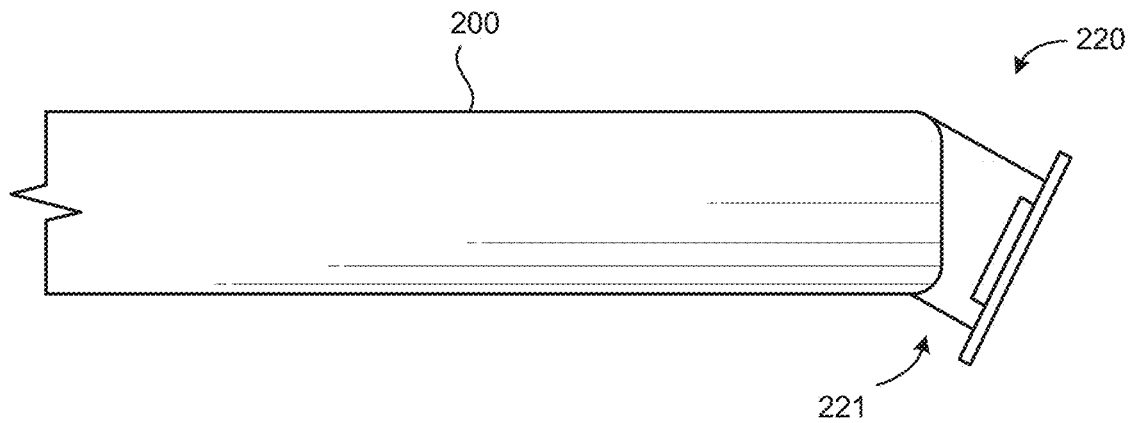
FIG. 10A illustrates a side view of an elongate fixation member with an angled cap attached thereto, according to an embodiment of the present disclosure.

FIG. 10A illustrates an elongate fixation member 200 with an angled cap 220 attached thereto at an angle with respect to the elongate fixation member 200. In this embodiment, a bottom surface 221 of the angled cap 220 may act to press downward on a flexible tensioning element (not shown) that may be coupled to the bottom surface 221 of the angled cap 220. This may further tension the flexible tensioning element and preload a bone fracture in compression to resist tensile/distraction forces that may be imparted across the bone fracture, as previously described herein.

Figure 10B:
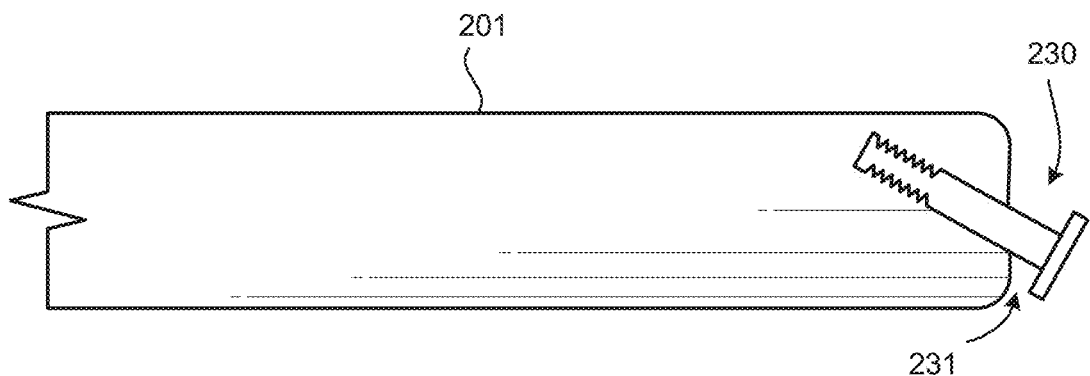
FIG. 10B illustrates a side view of an elongate fixation member with an angled fastener attached thereto, according to an embodiment of the present disclosure.
Figure 10C:
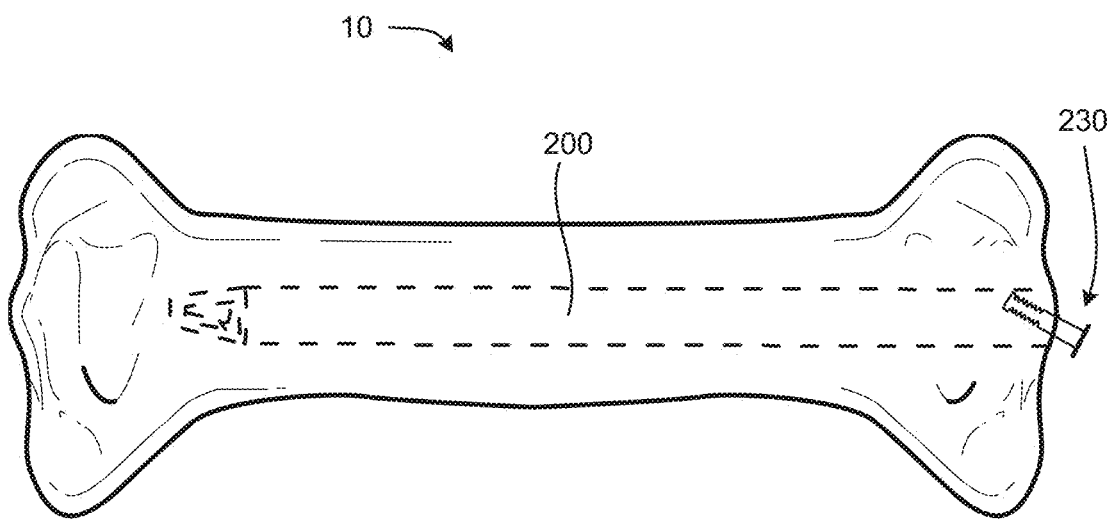
FIG. 10C illustrates a side view of the elongate fixation member of FIG. 10B inserted into a bone.

FIG. 10B illustrates an elongate fixation member 201 with an angled fastener 230 attached thereto at an angle with respect to the elongate fixation member 201. In this embodiment, a bottom surface 231 of the angled fastener 230 may likewise act to press downward on a flexible tensioning element (not shown) that may be coupled to the bottom surface 231 of the angled fastener 230. This may further tension the flexible tensioning element and preload a bone fracture in compression to resist tensile/distraction forces that may be imparted across the bone fracture, as previously described herein. FIG. 10C illustrates the elongate fixation member 201 and the angled fastener 230 inserted into a bone 10.

Figure 11A:
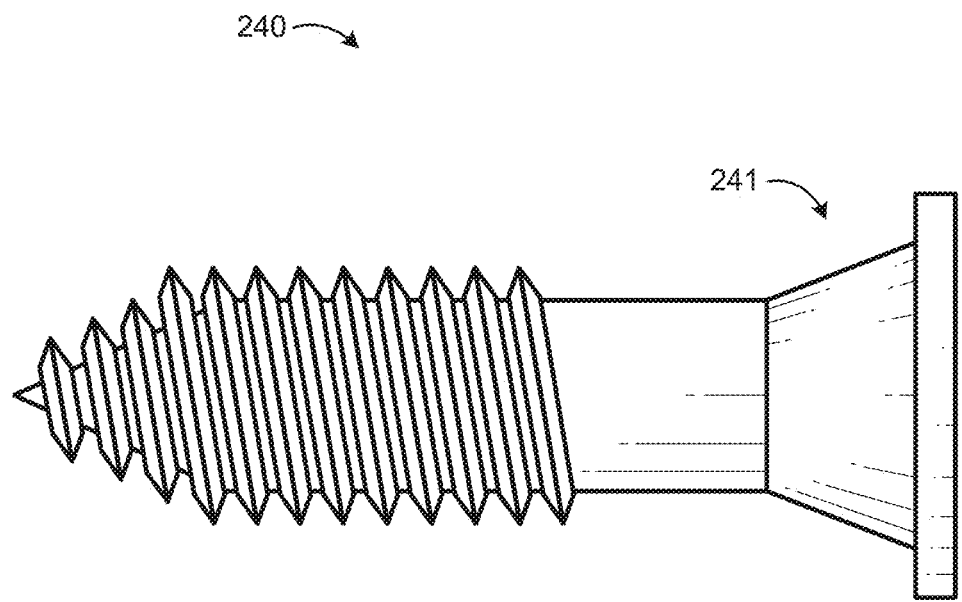
FIG. 11A illustrates a side view of flared fastener, according to an embodiment of the present disclosure.

FIG. 11A illustrates a flared fastener 240 comprising a flared portion 241 near the head of the flared fastener 240. In this manner, the flared fastener 240 may be coupled with an elongate fixation member (not shown) without the need of angling the flared fastener 240 with respect to the elongate fixation member, due to the inherent angle already created by the flared portion 241. In this embodiment, the flared portion 241 may act to press on a flexible tensioning element (not shown) as the flared fastener 240 couples with an elongate fixation member. This may further tension the flexible tensioning element and preload a bone fracture in compression to resist tensile/distraction forces that may be imparted across the bone fracture, as previously described herein.

Figure 11B:
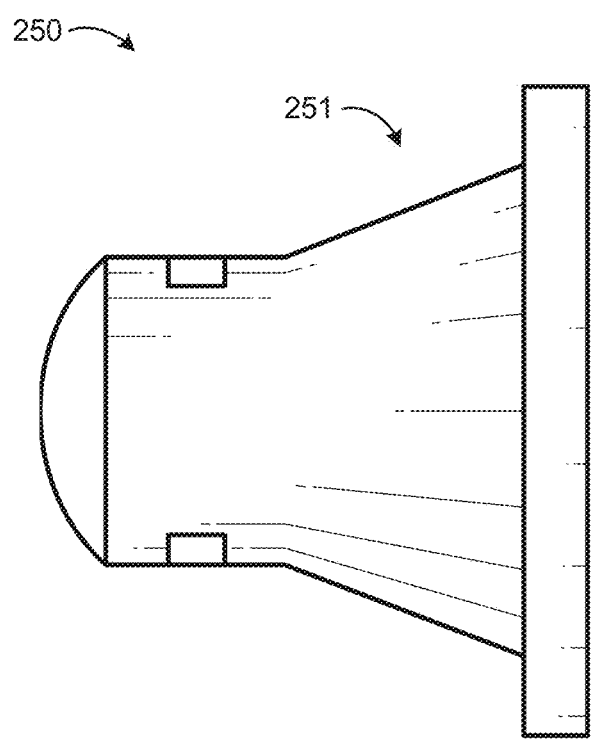
FIG. 11B illustrates a side view of flared cap, according to an embodiment of the present disclosure.

FIG. 11B illustrates a flared cap 250 comprising a flared portion 251 near the head of the flared cap 250. In this manner, the flared cap 250 may likewise be coupled with an elongate fixation member (not shown) without the need of angling the flared cap 250 with respect to the elongate fixation member, due to the inherent angle already created by the flared portion 251. In this embodiment, the flared portion 251 may likewise act to press on a flexible tensioning element (not shown) as the flared cap 250 couples with an elongate fixation member. This may further tension the flexible tensioning element and preload a bone fracture in compression to resist tensile/distraction forces that may be imparted across the bone fracture, as previously described herein.

Any procedures or methods disclosed herein may comprise one or more steps or actions for performing the described procedures or methods. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, drawing, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single embodiment disclosed herein.

Recitation of the term "first" with respect to a feature or element does not necessarily imply the existence of a second or additional such feature or element. Elements recited in means-plus-function format are intended to be construed in accordance with 35 U.S.C. § 112 (f). It will be apparent to those having skill in the art that changes may be made to the details of the above-described embodiments without departing from the underlying principles set forth herein.

The phrases "connected to," "coupled to," and "in communication with" refer to any form of interaction between two or more entities, including mechanical, electrical, magnetic, electromagnetic, fluid, and thermal interaction. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described herein, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A bone fixation assembly comprising:
    an elongate fixation member comprising:
        a central longitudinal axis;
        a first portion couplable within a first intramedullary canal of a first bone fragment of a bone;
        a second portion couplable within a second intramedullary canal of a second bone fragment of the bone to provide fixation of the second bone fragment relative to the first bone fragment;
        a first transverse passageway formed through the first portion of the elongate fixation member; and
        a second transverse passageway formed through the second portion of the elongate fixation member; and
    a flexible tensioning element couplable to the first and second portions of the elongate fixation member to secure the elongate fixation member to the bone, the flexible tensioning element comprising:
        a first tension band couplable to the first portion of the elongate fixation member through the first transverse passageway; and
        a second tension band couplable to the second portion of the elongate fixation member through the second transverse passageway,
    wherein:
        the first transverse passageway is configured to receive the flexible tensioning element therethrough from a first direction transverse to the central longitudinal axis of the elongate fixation member;
        the second transverse passageway is configured to receive the flexible tensioning element therethrough from a second direction transverse to the central longitudinal axis of the elongate fixation member; and
        the flexible tensioning element is configured to span a bone fracture intermediate the first bone fragment and the second bone fragment to preload the bone fracture in compression to resist tensile force imparted across the bone fracture, thereby maintaining fixation of the first bone fragment relative to the second bone fragment.

2. The bone fixation assembly of claim 1, wherein a first end of the flexible tensioning element is couplable with a second end of the flexible tensioning element to secure the elongate fixation member to the bone.

3. The bone fixation assembly of claim 1, wherein the first and second tension bands are couplable to each other to secure the elongate fixation member to the bone.

4. The bone fixation assembly of claim 3, wherein a first end of the first tension band is couplable with a second end of the second tension band, and a second end of the first tension band is couplable with a first end of the second tension band to form a crisscross pattern that spans the bone fracture and secures the elongate fixation member to the bone.

5. The bone fixation assembly of claim 1 comprising a securing element couplable to the flexible tensioning element and configured to prevent loosening of the flexible tensioning element.

6. The bone fixation assembly of claim 1 comprising a tensioner element couplable to the flexible tensioning element and configured to impart a tension force to the flexible tensioning element.

7. A bone fixation assembly comprising:
    an elongate fixation member comprising:
        a central longitudinal axis;
        a distal portion couplable to a first bone fragment of a bone; and
        a proximal portion couplable to a second bone fragment of the bone to provide fixation of the second bone fragment relative to the first bone fragment; and
    a flexible tensioning element couplable to the proximal portion and the distal portion of the elongate fixation member to secure the elongate fixation member to the bone, the flexible tensioning element comprising:
        a first tension band couplable to the distal portion of the elongate fixation member; and
        a second tension band couplable to the proximal portion of the elongate fixation member and to the first tension band to secure the elongate fixation member to the bone,
        wherein the flexible tensioning element is configured to span a bone fracture intermediate the first bone fragment and the second bone fragment to preload the bone fracture in compression to resist tensile force imparted across the bone fracture, thereby maintaining fixation of the first bone fragment relative to the second bone fragment.

8. The bone fixation assembly of claim 7, wherein a first end of the flexible tensioning element is couplable with a second end of the flexible tensioning element to secure the elongate fixation member to the bone.

9. The bone fixation assembly of claim 7, wherein a surface of the elongate fixation member comprises one or more channels configured to receive the flexible tensioning element therein to secure the elongate fixation member to the bone.

10. The bone fixation assembly of claim 7, wherein the elongate fixation member comprises:
    a first transverse passageway formed through the distal portion of the elongate fixation member, wherein the first transverse passageway is configured to receive the first tension band therethrough from a first direction transverse to the central longitudinal axis of the elongate fixation member; and
    a second transverse passageway formed through the proximal portion of the elongate fixation member, wherein the second transverse passageway is configured to receive the second tension band therethrough from a second direction transverse to the central longitudinal axis of the elongate fixation member.

11. The bone fixation assembly of claim 7, wherein the elongate fixation member comprises a longitudinal passageway configured to receive the flexible tensioning element therethrough.

12. The bone fixation assembly of claim 7 comprising a securing element couplable to the flexible tensioning element and configured to prevent loosening of the flexible tensioning element.

13. The bone fixation assembly of claim 7 comprising a tensioner element couplable to the flexible tensioning element and configured to impart a tension force to the flexible tensioning element.

14. A method of fixing a first bone fragment of a bone relative to a second bone fragment of the bone, the method comprising:
 forming one or more first bone tunnels in the first bone fragment comprising at least one of:
  forming a first transverse bone tunnel in the first bone fragment; and
  forming a first longitudinal bone tunnel in a first intramedullary canal of the first bone fragment;
 forming one or more second bone tunnels in the second bone fragment comprising at least one of:
  forming a second transverse bone tunnel in the second bone fragment; and
  forming a second longitudinal bone tunnel in a second intramedullary canal of the second bone fragment;
 coupling a first portion of an elongate fixation member to the first bone fragment;
 coupling a second portion of the elongate fixation member to the second bone fragment to provide fixation of the second bone fragment relative to the first bone fragment;
 passing a flexible tensioning element through the one or more first bone tunnels and the one or more second bone tunnels;
 coupling the flexible tensioning element to the first portion of the elongate fixation member and the second portion of the elongate fixation member to secure the elongate fixation member to the bone; and
 spanning a bone fracture intermediate the first bone fragment and the second bone fragment with the flexible tensioning element to preload the bone fracture in compression to resist tensile force imparted across the bone fracture, thereby maintaining fixation of the first bone fragment relative to the second bone fragment.

15. The method of claim 14, wherein:
 coupling the first portion of the elongate fixation member to the first bone fragment comprises coupling the first portion of the elongate fixation member within the first intramedullary canal of the first bone fragment; and
 coupling the second portion of the elongate fixation member to the second bone fragment comprises coupling the second portion of the elongate fixation member within the second intramedullary canal of the second bone fragment.

16. The method of claim 14, wherein:
 coupling the first portion of the elongate fixation member to the first bone fragment comprises coupling the first portion of the elongate fixation member to a first surface of the first bone fragment; and
 coupling the second portion of the elongate fixation member to the second bone fragment comprises coupling the second portion of the elongate fixation member to a second surface of the second bone fragment.

17. The method of claim 14 further comprising:
 coupling a first end of the flexible tensioning element with a second end of the flexible tensioning element to secure the elongate fixation member to the bone.

* * * * *